United States Patent [19]
Ts'o et al.

[11] Patent Number: 5,994,517
[45] Date of Patent: Nov. 30, 1999

[54] LIGANDS TO ENHANCE CELLULAR UPTAKE OF BIOMOLECULES

[75] Inventors: Paul O. P. Ts'o, 3400 N. Charles St., Baltimore, Md. 21218; Jon J. Hangeland, Morrisville, Pa.; Yuan C. Lee, Baltimore, Md.

[73] Assignee: Paul O. P. Ts'o, Baltimore, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/755,062

[22] Filed: Nov. 22, 1996

Related U.S. Application Data

[60] Provisional application No. 60/007,480, Nov. 22, 1995.

[51] Int. Cl.[6] .................................................. C07K 16/00
[52] U.S. Cl. .................................... 530/391.9; 530/391.7; 530/395; 536/23.1
[58] Field of Search .............................. 530/391.7, 391.9, 530/395; 536/23.1

[56] References Cited

PUBLICATIONS

Bonfils, et al, 1994, "Drug targeting: Synthesis and endocytosis of . . . " Nucleic Acids Res. 20(17): 4621–29.
Zaia, et al, 1988, "Inhibition of human immunodeficiency virus by . . . " J. Virol. 62(10): 3914–3917.
Merwin, et al, 1994, "Targeted Delivery of DNA Using . . . " Bioconjugate Chem. 5: 612–620.
Agris, et al, 1986, "Inhibition of vesicular Stomatitis Virus . . . " Biochemistry 25: 6268–6275.

*Primary Examiner*—Jeffrey Stucker
*Attorney, Agent, or Firm*—Pillsbury Madison & Sutro LLP

[57] ABSTRACT

Oligodeoxynucleoside methylphosphonate neoglycopeptide conjugates and related compounds for tissue specific delivery of biologically stable, nonionic oligodeoxynucleoside analogs into cells.

17 Claims, 13 Drawing Sheets

[a] Sugar may be, but is not restricted to, any of the following sugars: glucose, N-acetylglucosamine, galactose, N-acetylgalactose, mannose, fucose.
[b] Folic acid may be used in place of the sugar residues.

a Sugar may be, but is not restricted to, any of the following sugars: glucose, N-acetylglucosamine, galactose, N-acetylgalactose, mannose, fucose.
b Folic acid may be used in place of the sugar residues.

3"dT 5'-CPG

→ Alternating couplings with 2'-OCH₃ methylphosphonate and 2'-OCH₃ phosphodiester synthons 5'(2'-OMe-ApGpUpCpApGpUpCpApGpU)dT* ps 3'-3'dTpsdT 5'-CPG → C6-Disulfide cyanoethylphosphoamidite synthon DMTO-(CH₂)₆-SS-(CH₂)₆ ps 5'(2'-OMe-ApGpUpCpApGpUpCpApGpU)dT* ps 3'-3'dTpsdT 5'-CPG 10: [YEE(ah-GalNAc)$_3$]-SMCC-AET-pU$^m$pT$_7$ 12: [YEE(ah)$_3$]-SMCC-AET-pU$^m$pT$_7$ 3: [Y]-SMCC-AET-pU$^m$pT$_7$ 4: pU$^m$pT$_7$ 5: [YEE(ah-GalNAc)$_2$]-SMCC-AET-pU$^m$pT$_7$ 6: [YEE(ah-GalNAc)$_3$]-SMCC-AET-pU$^m$

LIGANDS TO ENHANCE CELLULAR UPTAKE OF BIOMOLECULES

This application is based on U.S. Provisional Application No. 60/007,480, filed Nov. 22, 1995.

BACKGROUND OF THE INVENTION

1. Field of the Invention

This invention relates to a delivery system for introducing homogeneous oligonucleoside conjugates that are resistant to biodegradation into cells in a tissue specific manner via ligand directed, receptor mediated, endocytosis pathway.

2. Background Information

The antisense (anticode) or antigene strategy for drug design is based on the sequence-specific inhibition of protein synthesis due to the binding and masking of the target mRNA or genomic DNA, respectively, by the synthetic oligodeoxynucleotides (oligo dN) and their analogs (1). Implicit in this strategy is the ability of oligo-dns to cross cellular membranes, thereby gaining access to the cellular compartments containing their intended targets, and to do so in sufficient amounts for binding to those targets to take place. Among the many oligo-dn analogs for application as antisense, non-ionic oligonucleoside methylphosphonates (oligo-MPs) have been extensively studied (2). Oligo-MPs are totally resistant to nuclease degradation (3) and are effective antisense agents with demonstrative in vitro activity against herpes simplex virus type 1 (4), vesicular stomatitis virus (5) and human immunodeficiency virus (6), and are able to inhibit the expression of ras p21 (7). For oligo-MPs to exhibit antisense activity, however, they must be present in the extracellular medium in concentrations up to 100 $\mu$M (4–7). Achieving and maintaining these concentrations for therapeutic purposes presents a number of difficulties, including expense, potential side effects owing to non-specific binding of the oligo-MP and immunogenicity. These difficulties can be circumvented in two ways:

1) By enhancing transport of the oligo-MP across the membrane of the targeted cell line achieving a locally high concentration of the oligo-MP.

2) By specific delivery to a target cell line only, thereby avoiding toxic side effects to other tissues.

Both strategies serve to greatly reduce the concentration of the oligo-MP needed to produce an antisense effect and to avoid the toxic side effect with tissue specificity.

Delivery of exogenous DNA into the intracellular medium is greatly enhanced by coupling its uptake to receptor-mediated endocytosis. Pioneering work by Wu and Wu (8) showed that foreign genes (8a–c) or oligo-dns (8d), electrostatically complexed to poly-L-lysine linked to asialoorosomucoid, are efficiently and specifically taken into human hepatocellular carcinoma (Hep G2) cells through direct interaction with the asialoglycoprotein receptor. Since this initial study, other examples of receptor-mediated delivery of DNA have appeared including a tetra-antennary galactose neoglycopeptide-poly-L-lysine conjugate (9), a trigalactosylated bisacridine conjugate (10), folate conjugates (11), an antibody conjugate (12), transferrin conjugate (13) and 6-phosphomannosylated protein linked to an antisense oligo-dns via a disulfide bond (14). Recently, the tri-antennary N-acetylgalactosamine neoglycopeptide, YEE (ah-GalNAc)$_3$ (15), conjugated to human serum albumin which was in turn linked to poly-L-lysine was shown to effectively deliver DNA into Hep G2 cells (16). While improved, these methods of delivery have several disadvantages: (1) by virtue of the structural heterogeneity of the starting materials (e.g. most often poly-L-lysine or bovine serum albumin) and the synthetic strategies employed, glycoconjugates derived from these materials are functionally equivalent, but structurally heterogeneous, therefore, their physical and biological properties would be difficult to fully define; (2) polycationic compounds (e.g. poly-L-lysine and cationic lipids) are toxic at concentrations employed for the delivery of DNA and oligo-dns in vitro and presumably in vivo; (3) the ratio of oligo-dN or DNA to cationic conjugate must be empirically determined in each case.

A number of synthesis products have been described for the delivery of oligo dN which are heterogeneous mixtures of conjugates. Bonfils et al., for example, describe formation of conjugates between 6-phosphomannosylated protein and oligonucleosides which, because the modification of the protein and the formation of the disulfide link are not regiochemically controlled, yields a mixture of functionally related but structurally different molecules.

Several studies have described intracellular delivery of oligodeoxynucleotides or DNA which contain biodegradable phosphodiester internucleotide linkages. Because of this, they may have relatively short half lives within the cell and efficacy is consequently reduced. For example, an all phosphodiester 16-mer, d(T)$_{16}$, was extensively degraded after only two hours in the cell. This disadvantage with oligo-dNs and DNA is well recognized in the antisense community. The present invention enables the delivery of biologically stable oligo-MPs, other oligodeoxynucleotide analogs (see Table 1) and other biostable pro-drugs using the delivery strategy described herein. Thus, a further reduction in the concentration of the antisense agent can be realized as a consequence of its biostability.

Merwin et al. describe the synthesis of conjugates using neoglycopeptide YEE(ah-GalNAc)$_3$. Their delivery system is heterogeneous and contains poly-L-lysine, which serves to electrostatically bind DNA to the conjugate. The disadvantages of this delivery strategy are: its structural heterogeneity; potential toxicity due to its polycationic charge; and difficulties in formulation due to the need to empirically determine the ratio of cationic carrier to oligo-dn or DNA for optimum delivery. The delivery strategy of the present invention obviates all these difficulties because it is chemically defined and structurally homogeneous and it is intended to deliver biologically stable antisense agents and other biostable pro-drugs.

Thus, conjugates available heretofor for delivering oligo dN and oligo dN analogs to their intracellular targets suffer from the disadvantage of being heterogeneous and/or rapidly biodegradable, with the consequences that the most efficacious compounds may be delivered in a dilute form to the target along with extraneous compounds which may be ineffective and/or harmful.

SUMMARY OF THE INVENTION

It is an object of the invention to provide homogeneous oligodeoxynucleoside methylphosphonate conjugates, which contain non-biodegradable methylphosphonate internucleotide linkages. This enables the delivery of biologically stable, nonionic oligodeoxynucleoside analogs into cells.

It is a further object of the invention to provide a method for synthesizing conjugates of oligodeoxynucleoside chimeras that contain all 2'-O-methylribose nucleosides and internucleotide linkages that alternate between methylphosphonate and phosphodiester or any other biostable oligomers. Such biostable oligomers include, but are not limited to, oligodeoxynucleotide analogs that contain: all 2'-deoxyribose nucleosides and internucleotide linkages that alternate between phosphorothioate and methylphosphonate; all 2'-deoxyribose nucleosides and phosphorothioate internucleotide linkages; all 2'-O-methylribose and phosphorothioate internucleotide linkages.

It is a further object of the invention to provide biologically non-degradable (or hydrolytic enzyme resistant) conjugates comprising oligo dN and/or oligo dN analogs which can efficiently cross cellular membranes and gain access to the cytoplasm. The term "efficiently", as used herein, is intended to mean that, for example, if the conjugate is present in the extracellular medium, then following a 24 hour incubation period at 37° C., the intracellular concentration will be at least approximately 3 times and preferably approximately 10 times the extracellular concentration.

It is a further object of the invention to provide a structurally defined and chemically uniform "Delivery Assembly" which consists of ligand-linker-pro-drug for a tissue/cell type specific, ligand directed, receptor-mediated endocytotic delivery of a drug which is not biodegradable in the target cells/tissues. The linkage between ligand and pro-drug is covalent, and is formed through a crosslinking reagent, which is capable of forming covalent bonds with the ligand and the pro-drug. A wide variety of cross-linking reagents are available that are capable of reacting with various functional groups present on the ligand and the pro-drug, thus, many chemically distinct linkages can be constructed. For example, the ligand YEE(ah-GalNAc)$_3$ (see 1; FIG. 1) contains a free amino group at its amino terminus. It will react regiospecifically with the heterobifunctional cross-linking reagent, SMCC (entry 3; Table 4), to form an amide bond. The pro-drug, if chemically modified to contain a free sulhydryl group (for examples see entries 9–14, Table 2) will chemically combine with SMCC to form a thioether linkage. In this example, the linkage formed between the ligand and pro-drug could be summarized as amide/thioether. It is apparent that hundreds of structures can be formulated by combining the ligands, cross-linking reagents and pro-drugs (illustrated in Tables 1–4 and FIG. 1) in all of the possible combinations. Thus other linkages include, but are not restricted to, amide/amide, thioether/amide, disulfide/amide, amide/thioether, amide/disulfide. The linkages can be further categorized as biologically stable (thioether, amine), somewhat biologically stable (amide), and biologically labile (disulfide). Thus, the delivery system can be modified structurally to function in the various chemical environments encountered in the extra- and intracellular medium. The ligands for this delivery system include, but are not restricted to those shown in FIG. 1. The term "attachment groups", as used herein, refers to these ligands. The ligands consist of a synthetic, chemically defined, structurally homogeneous oligopeptide scaffold that is glycosylated with any of a number of sugar residues including, but not restricted to: glucose; N-acetylglucosamine; galactose; N-acetylgalactosamine; mannose; and fucose. The term "neoglycopeptide", as used herein, refers to these and similar structures. In addition, these oligopeptides provide frameworks to construct multivalent ligands with folic acid.

The term "pro-drug", as used herein, means a compound that, upon hydrolysis or bioreduction of specific chemical linkage(s), is released from the conjugate to become active or more active than when contained as part of the conjugate.

The term "chemically uniform", as used herein, means that at least 95% of the delivery assembly, and most preferably 99%, is a single species both in composition and in connectivity. Determination of chemical uniformity is by polyacrylamide gel electrophoresis, reverse-phase high pressure liquid chromatography, nuclear magnetic resonance, mass spectrometry and chemical analysis. The phrase "chemically defined and structurally homogeneous" is used interchangeably with "chemically uniform".

The term "gene specific", as used herein, means that the pro-drug is an oligonucleoside (particularly an oligodeoxynucleoside methylphosphonate or analog thereof) having a sequence that is complementary to a portion of a gene or a portion of a mRNA molecule found in the tissue or cell type targeted by the conjugate. The formation of a sequence-specific duplex between a gene specific pro-drug and the target mRNA will lead to the suppression of expression of the mRNA.

BRIEF DESCRIPTION OF THE DRAWINGS

FIG. 10. Reaction scheme for the automated synthesis with 5'-thiol modifier.

DETAILED DESCRIPTION OF THE INVENTION

Abbreviations

Figure 1:
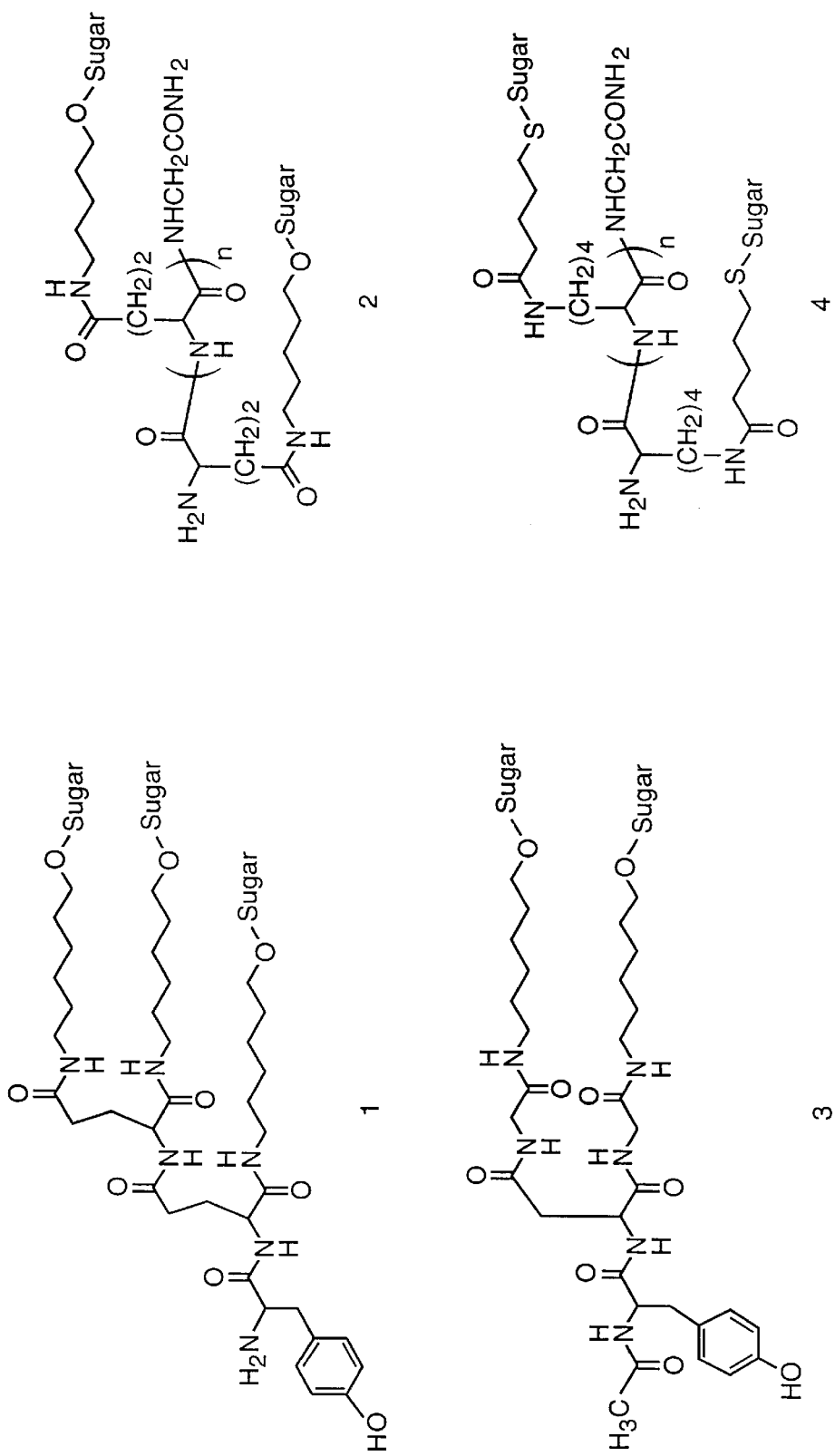
FIG. 1. Attachment groups for chemically uniform conjugates. The value of n is between 0 and 10, inclusive.

For convenience, the following abbreviations are used: AET, 2-aminomercaptoethanol (aminoethanethiol); ATP, adenosine triphosphate; BAP, bacterial alkaline phosphatase; CPG, controlled pore glass support; DIPEA, diisopropylethylamine; D-MEM, Dulbecco's modified Eagle's medium; DMSO, dimethyl sulfoxide; D-PBS, Dulbecco's phosphate buffered saline; DTT, dithiothreitol; EDAC, 1-ethyl-3-[3(dimethylamino)propyl] carbodiimide; EDTA, ethylenediaminetetraacetate; FCS, fetal calf serum; GalNAc, N-acetylgalactosamine; MEM, minimal essential medium with Earle's salts; SMCC, N-hydroxysuccinimidyl 4 (N-methylmaleimido)cyclohexyl-1 carboxylate; Tris, tris (hydroxymethyl)amine.

Synthesis of $[5'-^{32}p]$-[YEE(ah-GalNAc)$_3$]-SMCC-AET-pU$^m$pT$_7$ (10). Materials.

Methylphosphonamidite synthons were a generous gift from JBL Scientific, Inc., and are commercially available. They can readily synthesized from the nucleoside according to established procedures by an ordinarily skilled practitioner. All other reagents for the automated synthesis of U$^m$pT$_7$ were purchased from Glen Research, Inc. HiTrap Q anion exchange columns were purchased from Pharmacia LKB Biotechnology. Reverse phase high performance liquid chromatography was carried out using Microsorb C-18 column purchased from Rainin Instrument Co., Inc. Cystamine hydrochloride, 1-ethyl-3-[3-(dimethylamino)propyl] carbodiimide (EDAC), 1-methylimidazole, and anhyd. dimethylsulfoxide (DMSO), dithiothreitol (DTT), and Ellmen's reagent were purchased from Aldrich and were used without further purification. Diisopropylethylamime (DIPEA) was purchased from Aldrich and was redistilled from calcium hydride prior to use. N-Hydroxysuccinimidyl-4-(N-methylmaleimido)cyclohexyl carboxylate (SMCC) was purchased from Pierce. Waters SepPak C-18 cartridges were purchased from Millipore Corp. YEE(ah-GalNAc)$_3$ was synthesized according to Lee et al. (15a) and was stored at 4° C. as an aqueous solution. Adenosine triphosphate (ATP) and [γ-$^{32}$p]-ATP were purchased from P-L Biochemicals, Inc. and Amersham, respectively. Polyacrylamide gel electrophoresis (PAGE) was carried out with 20 cm×20 cm×0.75 mm gels which contained 15% polyacrylamide, 0.089 M Tris, 0.089 M boric acid, 0.2 mM EDTA (1× TBE) and 7 M urea. Samples were dissolved in loading buffer containing 90% formamide, 10% 1× TBE, 0.2% bromophenol blue and 0.2% xylene blue.

EXAMPLE 1

Synthesis of U$^m$pT$_7$ (6).

The oligodeoxynucleoside methylphosphonate was synthesized on a controlled pore glass support (CPG) using 5'-O-(dimethoxytrityl)-3'-O-methyl-N,N-diisopropylphosphonamidite thymidine and deprotected according to established methods (17). The final synthon incorporated into the oligomer at its 5' end was 5'-O-(dimethoxytrityl)-2'-O-methyl-3'-[(2-cyanoethyl)-N,N-diisopropyl]phosphorami dite uridine. The final coupling step positioned a phosphodiester linkage between the terminal 5' nucleoside and the adjacent nucleoside which permitted phosphorylation of the 5' terminal hydroxyl group with bacteriophage T4 polynucleotide kinase and ensured reasonable stability of the phosphodiester due to the presence of the 2'-O-methyl group. The crude 8-mer was purified by HiTrap Q anion exchange chromatography (load with buffer containing <25% acetonitrile; elute with 0.1 M sodium phosphate, pH 5.8) and preparative reverse phase chromatography (Microsorb C-18) using a linear gradient (Solvent A: 50 mM sodium phosphate, pH 5.8, 2% acetonitrile; Solvent B: 50 mM sodium phosphate, pH 5.8, 50% acetonitrile; gradient: 0–60% B in 30 min). The oligomer thus purified was ca 97% pure by analytical HPLC, only contaminated by a small amount of the n-1 species.

EXAMPLE 2

Synthesis of $[5'-^{32}P]$-5'-O-[(N-2-thioethyl)phosphoramidate]-U$^m$p$_7$ (9).

The purified oligomer (168 nmol), ATP (160 nmol), H$_2$O (75 μL), 10× PNK buffer (5 mM DTT, 50 mM Tris•HCl, 5 mM MgCl$_2$, pH 7.6; 10 μL), [γ-$^{32}$p]-ATP (3000 Ci/mmol, 100 Cci, 10 μL), and PNK (150 U in 5 μL) were combined and incubated at 37° C. for 16 h and evaporated to dryness. The residue was redissolved in 0.2 M 1-methylimidazole, pH 7.0 (100 μL) and 1.0 M cystamine hydrochloride, pH 7.2, containing 0.3 M EDAC (100 μL) and heated at 50° C. for 2 h (18). The excess reagents were removed by SepPak (loaded with 50 mM sodium phosphate, pH 5.8, 5% acetonitrile; washed with 5% acetonitrile in water; eluted with 50% acetonitrile in water). The solvent was evaporated in vacuo and crude cystamine adduct redissolved in 10 mM phosphate containing 50 mM DTT (200 mL) and heated to 37° C. for 1 h. The buffer salts and the excess reductant were removed from the reaction mixture as before and the crude product was dried in vacuo. The title compound 9, produced in 57% yield from 6, was used in the next step without further purification.

EXAMPLE 3

Synthesis of $[5'-^{32}p]$-[YEE(ah-GalNAc)$_3$]-SMCC-AET-pU$^m$pT$_7$ (10).

The neoglycopeptide 5 (336 nmol) was dissolved in anhyd. DMSO (40 μL) and treated with DIPEA (336 nmol) and SMCC (336 nmol). The reaction was allowed to stand at r.t. for 4 h, then added to the freshly prepared thiol 9. The reaction mixture was degassed and allowed to slowly concentrate under vacuum at r.t. The crude 10 was dissolved in formamide loading buffer (100 μL), purified by PAGE (4 V/cm, 1.5 h), and recovered by the crush and soak method (50% acetornitrile in water). The overall yield of pure 10 was 25%. 10 produced [5'-$^{32}$P]-phosphorylated 6 upon treatment with 0.1 N HCl (37° C., 1 h) due to hydrolysis of the P-N bond; however, 6 was unreactive towards DTT (50 mM, pH 8, 37° C., 1 h), 3-maleimidopropionic acid (50 mM, pH 8, 37° C., 1 h), Ellman's reagent (50 mM, pH 8, 37° C., 1 h) and BAP (70 U, 65° C., 1 h). Sequential treatment of 10 with 0.1 N HCl and BAP resulted in complete loss of [$^{32}$p]-label as anticipated. Stoichiometric analysis of an unlabeled sample of 10 prepared in an identical manner showed it to contain 3 mol of N-acetylgalactosamine for each mol of conjugate, consistent with the proposed structure. (The molar absorptivity of UpT$_7$ was calculated to be 59,750 L/mol-cm by taking the sum of the molar absorptivity values for each of the nucleosides contained in the structure. This value was in excellent agreement with the number of moles of GalNAc residues found contained in the conjugate.) Pneumatically assisted electrospray mass spectrometry produced a parent ion (negative ion mode) at M/Z 4080 (calculated mass 4080.7).

Cellular Uptake Experiments.

Materials.

Minimal essential medium with Earle's salts supplemented with L-glutamine (MEM), Dulbecco's modified Eagle's medium (D-MEM), RPMI medium 1640 supplemented with L-glutamine (RPMI), Dulbecco's phosphate buffered saline (D-PBS), fetal calf serum (FCS), sodium pyruvate (100 mM), non-essential amino acids (10 mM), aqueous sodium bicarbonate (7.5%), and trypsin (0.25%; prepared in HBSS with 1.0 mM EDTA) were purchased from GIBCO BRL. Human hepatocellular carcinoma (Hep G2), human fibrosarcoma (HT 1080), and human promyelocytic leukemia (HL-60) cells were purchased from ATCC and were maintained in 1× MEM supplemented with 10% FCS, 1 mM sodium pyruvate, and 0.1 mM non-essential amino acids (Hep G2), 1× D-MEM supplemented with 10% FCS (HT-1080), or 1× RPMI supplemented with 10% FCS (HL-60). Silicon oil was a gift from General Electric (product no. SF 1250). Cells were counted using a Coulter Cell Counter.

EXAMPLE 4

Uptake Experiments with Hep G2 Cells or HT 1080.

Cells were passaged into 2 cm wells and grown in the appropriate medium to a density of ca. 10$^5$ cells per well. The maintenance media was aspirated and the cells were incubated at 37° C. with 0.5 mL medium that contained 2% FCS and was made 1 μM in [5'-$^{32}$p]-labeled 10. After the prescribed time had elapsed, a 5 μL aliquot of the media was saved for scintillation counting and the remainder aspirated from the well. The cells were washed with D-PBS (2×0.5 mL), treated with 0.25% trypsin (37° C., 2 min) and suspended in fresh growth medium containing 10% FCS. The suspended cells were layered over silicon oil (0.5 mL) in a 1.7 mL conical microcentrifuge tube and pelleted by centrifugation at 14,000 rpm (12,000 g) for 30 sec. The supernatant was carefully decanted and the cell pellet was lysed with 100 μL of a solution containing 0.5% NP 40, 100 mM sodium chloride, 14 mM Tris-HCl and 30% acetonitrile. The amount of radioactivity, and by inference the amount of 10 associated with the cell lysate, was determined by scintillation counting.

EXAMPLE 5

Uptake Experiments with HL-60 Cells. RPMI medium supplemented with 2% FCS and made 1 μM in [γ-$^{32}$P]-10 was pre-treated with 7.5×10$^6$ HL 60 cells for 5 min at r.t. The cells were removed by centrifugation (5 min) The medium (31 mL) was decanted and added to 7.5×10$^6$ fresh HL 60 cells. The cells were evenly suspended and cell suspension divided into six 0.4 mL portions. The remainder was discarded. The cells were incubated for the prescribed time, then collected by centrifugation (5 min), resuspended in 0.5 mL D-PBS and layered onto silicon oil in a 1.7 mL conical microfuge tube. The cells were pelleted by centrifugation (12,000 g, 30 s), lysed, and the amount of [$^{32}$p]-labeled material associated with the cells determined by scintillation counting.

EXAMPLE 6

Methods for synthesizing additional conjugates.

The methods of the invention can be used to synthesize a wide variety of useful conjugates. Fourteen examples of oligonucleoside analogs are shown in Table 1. Table 2 lists 14 examples of 3'- and 5'-phosphate modification, which provide a 10 amine or a thiol for further reaction. Table 3 shows the neoglycopeptide, which contains a N-terminal amino group, and four methods for modifying the amine to provide a thiol. Finally, Table 4 lists several heterobifunctional cross-linking reagents and a Cathepsin D sensitive oligopeptide, which can be used to link the pro-drug to the ligand. It will be readily apparent that many other reagents are available which would be suitable.

In general, there are two reaction schemes that may be employed to covalently join the oligomer and neoglycopeptide. The first entails the coupling of an oligomer and the neoglycopeptide using a heterobifunctional cross-linking reagent and can be classified as a three component reaction. This scheme provides for complete regiochemical control of the coupling reaction and yields structurally defined and homogeneous conjugates. For example, if an oligomer of the type shown in Table 1, entry 1, were modified at its 5'-end with a thiol linker (Table 2, entry 10) post-synthetically and conjugated to YEE(ah-GalNAc)$_3$ (Table 3, entry 1) with SMCC (Table 4, entry 3), a conjugate with a linkage identical to the following would be obtained:

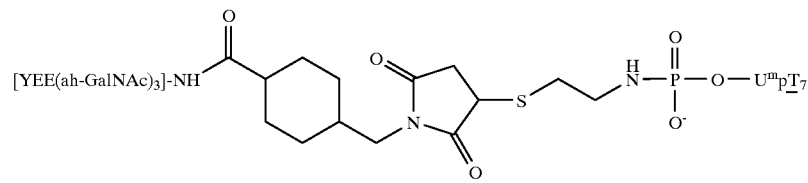

Alternatively, the neoglycopeptide can be modified as shown in Table 3, entries 2–5. Activation of the thiol may be accomplished using, for example, 2,2'-dipyridyl disulfide. Reaction of the activated thiol with any of the 3' or 5' thiol modified oligomers (Table 1, entries 9–14) would provide a disulfide linkage between the oligomer and the neoglycopeptide, as shown below:

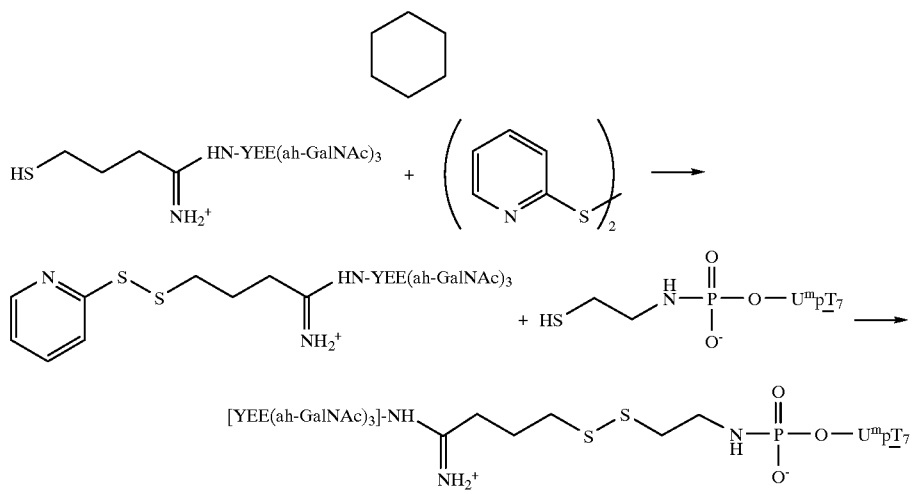

This second scheme provides access to disulfides with varying steric bulk around the sulfur atoms that are not accessible using commercially available crosslinking reagents (cf. Table 4, entries 4–6) Conceptually, this reaction scheme can be classified as a two component reaction in which one "half" of the conjugate is modified and then activated for reaction with the other "half".

TABLE 1

Oligonucleoside methylphosphonate analogs

| Entry | $R_1$ | $R_2$ | $R_3$ | $R_4$ |
|---|---|---|---|---|
| 1 | 5'-conjugate | H | H | H |
| 2 | H | H | H | 3'-conjugate |
| 3 | 5'-conjugate | —OCH$_3$ | —OCH$_3$ | H |
| 4 | H | —OCH$_3$ | —OCH$_3$ | 3'-conjugate |

TABLE 1-continued

Oligonucleoside methylphosphonate analogs

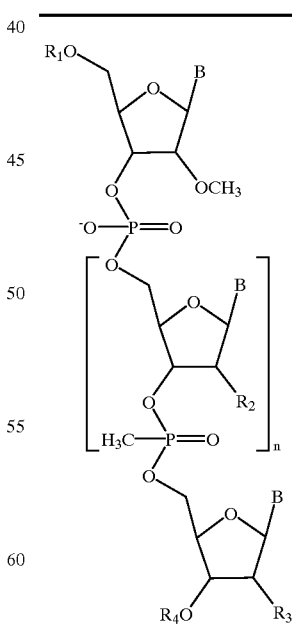

B = A, C, G, or T
$8 \leq n \leq 50$

TABLE 1-continued

Oligonucleoside methylphosphonate analogs

| Entry | $R_1$ | $R_2$ | $R_3$ | $R_4$ | $R_5$ |
|---|---|---|---|---|---|
| 5 | 5'-conjugate | $O^-$ | $CH_3$ | $O^-$ | H |
| 6 | H | $O^-$ | $CH_3$ | $O^-$ | 3'-conjugate |
| 7 | 5'-conjugate | $CH_3$ | $O^-$ | $CH_3$ | H |
| 8 | H | $CH_3$ | $O^-$ | $CH_3$ | 3'-conjugate |
| 9 | 5'-conjugate | $S^-$ | $CH_3$ | $S^-$ | H |
| 10 | H | $S^-$ | $CH_3$ | $S^-$ | 3'-conjugate |
| 11 | 5'-conjugate | $CH_3$ | $S^-$ | $CH_3$ | H |
| 12 | H | $CH_3$ | $S^-$ | $CH_3$ | 3'-conjugate |
| 13 | 5'-conjugate | $S^-$ | $S^-$ | $S^-$ | H |
| 14 | H | $S^-$ | $S^-$ | $S^-$ | 3'-conjugate |

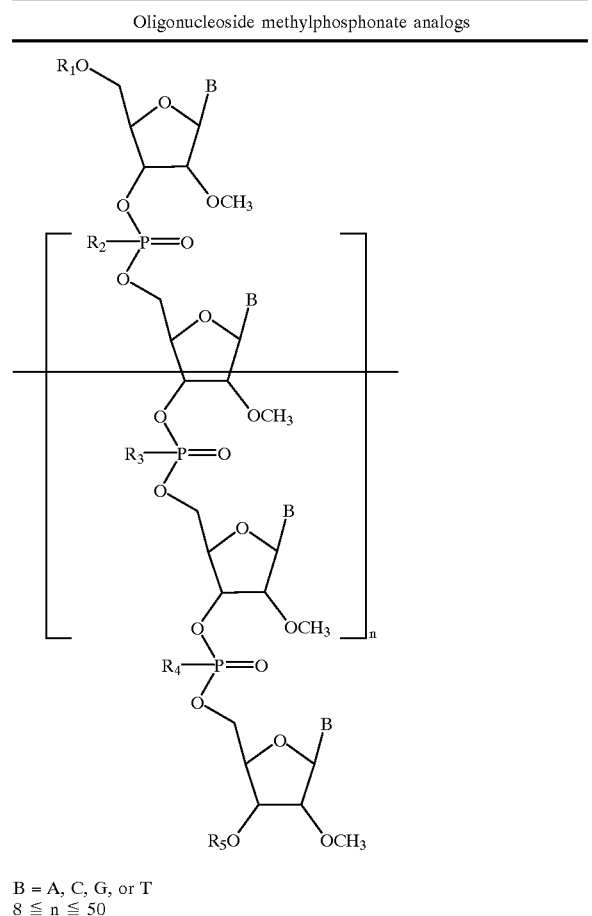

B = A, C, G, or T
$8 \leq n \leq 50$

TABLE 2

3' and 5' modified oligo-MPs for conjugation with neoglycopeptides

| Entry | Structure | Functional Group | Reactivity |
|---|---|---|---|
| 1–3 | 5'—P(=O)(O⁻)—O—(CH$_2$)$_n$—NH$_2$<br>n = 3, 6, 12 | amino | active esters isothiocyanates isocyanates aldehydes |
| 4 | 5'—P(=O)(O⁻)—O—CH$_2$CH$_2$—O—CH$_2$CH$_2$—NH$_2$ | amino | |
| 5 | 5'—P(=O)(O⁻)—NH—CH$_2$CH$_2$—NH$_2$ | amino | |

TABLE 2-continued

3' and 5' modified oligo-MPs for conjugation with neoglycopeptides

| Entry | Structure | Functional Group | Reactivity |
|---|---|---|---|
| 6 | (3'-phosphate-O-CH2-CH(CH2OH)-(CH2)4-NH2) | amino | |
| 7 | (3'-phosphate-O-CH2-CH(OH)-CH2-NH2) | amino | |
| 8 | (3'-phosphate-NH-CH2CH2-NH2) | amino | |
| 9 | (5'-phosphate-O-(CH2)6-SH) | thiol | 1° halides maleimides activated disulfides |
| 10 | (5'-phosphate-NH-CH2CH2-SH) | thiol | |
| 11 | (5'-phosphate-S⁻) | thiol | |
| 12 | (3'-phosphate-O-CH2CH2CH2-SH) | thiol | |
| 13 | (3'-phosphate-S⁻) | thiol | |
| 14 | (3'-phosphate-NH-CH2CH2-SH) | thiol | |

TABLE 3

Illustrations of functional group modifications to YEE(ah-GalNAc)$_3$[a]

| Entry | Modifying Reagent | Ligand | Reactive Group | Reactivity |
|---|---|---|---|---|
| 1 | none | H$_2$N-YEE(ah-GalNAc)$_3$ | amine | active esters isothiocyanates isocyanates aldehydes |

TABLE 3-continued

Illustrations of functional group modifications to YEE(ah-GalNAc)$_3$[a]

| Entry | Modifying Reagent | Ligand | Reactive Group | Reactivity |
|---|---|---|---|---|
| 2[b] | (substituted 2-iminothiolane structure with R$_1$, R$_2$, R$_3$) | (thiol-containing ligand with R$_1$, R$_2$, R$_3$ attached to YEE(ah-GalNAc)$_3$) | thiol | 1° halides maleimides activated disulfides |
| 3 | (γ-thiobutyrolactone) | HS-CH$_2$CH$_2$CH$_2$-C(=O)-HN-YEE(ah-GalNAc)$_3$ | thiol | |
| 4 | (S-acetyl succinic anhydride derivative) | (HS-substituted succinimide-N-YEE(ah-GalNAc)$_3$) | thiol | |
| 5 | (S-acetyl-NHS ester) | HS-CH$_2$CH$_2$-C(=O)-HN-YEE(ah-GalNAc)$_3$ | thiol | |

[a]These reagents may be used to modify any of the ligands illustrated in FIG. 1.
[b]See Goff, D. A.; Carroll, S. F. (1990) Substituted 2-iminothiolanes: reagents for the preparation of disulfide cross-linked conjugates with increased stability Bioconjugate Chem. 1, 381–386.

TABLE 4

Examples of possible combinations of activated oligo-MP, activated ligand and cross-linking reagent

| | Reactive Group | | | |
|---|---|---|---|---|
| Entry | Oligo-MP | Ligand | Cross-Linking Reagent | Linkage |
| 1 | —NH$_2$ | —NH$_2$ | (N$_3$-CH$_2$-C(=O)-NH-(CH$_2$)$_n$-C(=O)-CH(OCH$_3$)$_2$)[a] | amide/amine |
| 2 | —SH | —NH$_2$ | (4-(N-maleimido)benzoic acid NHS ester, MBS) | thioether/amide |

TABLE 4-continued

Examples of possible combinations of activated oligo-MP, activated ligand and cross-linking reagent

| Entry | Reactive Group Oligo-MP | Reactive Group Ligand | Cross-Linking Reagent | Linkage |
|---|---|---|---|---|
| 3 | —SH | —NH$_2$ | (structure) | thioether/amide |
| 4 | —SH | —NH$_2$ | (structure) | disulfide/amide |
| 5 | —SH | —NH$_2$ | (structure) | disulfide/amide |
| 6 | —SH | —NH$_2$ | (structure) | disulfide/amide |
| 7 | —NH$_2$ | —SH | see entries 2–6 | amide/thioether or amide/disulfide |
| 8 | —NH$_2$ | —NH$_2$ | α-citraconyl-K(ε-FMOC)PILFFRL[a] (cathepsin-D sensitive linker) | amide/amide |
| 9 | —SH | —SH | requires activation with 2,2'-dipyridyl disulfide or comparable reagent | disulfide |

[a]Reagents shown are not commercially available.

Discussion

Synthesis of [YEE(ah-GalNAc)$_3$]-SMCC-AET-pU$^m$pT$_7$ (10).

Figure 2:
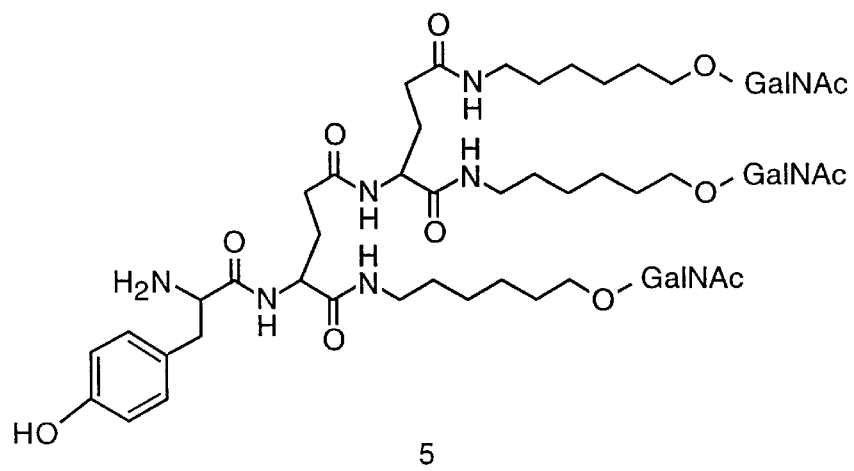
FIG. 2. Structures of neoglycopeptide YEE(ah-GalNAc)$_3$ (5) and oligo-MP U$^m$pT$_7$ (6), and 5'-ethylenediamine capped U$^m$pT$_7$ (11).
Figure 2:
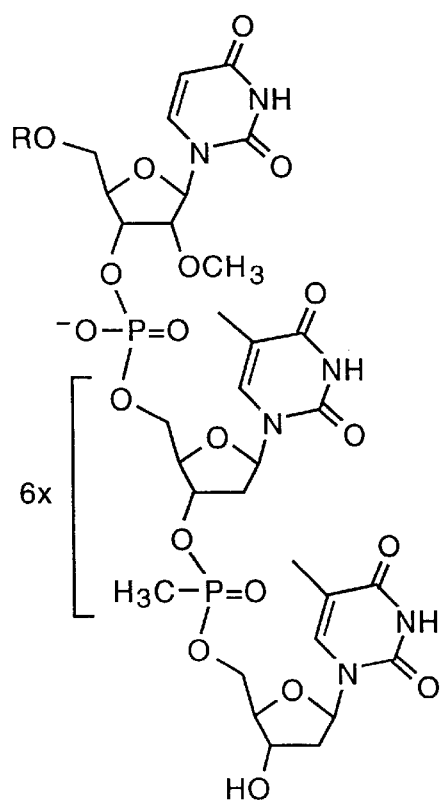

Synthesis and purification of YEE(ah-GalNAc)$_3$ (5) (15a) and U$^m$pT$^7$ (6) (17) was carried according to established procedures. In order to form a covalent link between 5 and 6, the 5' end of 6 was modified using the method of Orgel (18). This introduced a disulfide into the oligo-MP, which in turn could be reduced with DTT to give a 5'-thiol. The neoglycopeptide 5 was modified in a complementary fashion using the heterobifunctional cross-linking reagent, SMCC, capable of combining with the N-terminal amino group of 5. Coupling of the maleimido group introduced by SMCC and the 5'-thiol of the modified oligo-MP resulted in linkage of the oligo-MP and neoglycopeptide via a metabolically stable thioether (FIG. 2). To begin the synthesis, 6 was phosphorylated using T4 polynucleotide kinase and 0.95 equivalents of ATP. Formulation of the end-labeling reaction in this way ensured that ca. 90% of the ATP was consumed allowing efficient use of the [$^{32}$P]-ATP to radioactively label the conjugate. Modification of the 5' phosphate was accomplished in two steps. The end-labeled oligo-MP was incubated at 50° C. with 0.5 M cystamine hydrochloride in a buffer containing 0.1 M 1-methylimidazole at pH 7.2 in the presence of 0.15 M EDAC to give the 5' cystamine phosphoramidate in 65k yield. Up to 35% of thymidine-modified oligo-MP was produced during this reaction and, despite attempts to modify the reaction conditions (e.g., lowering the temperature and reducing the concentration of EDAC), its production could not be eliminated. This side product presumably arises due to reaction of EDAC with N-3 of thymidine to form a thymidine-EDAC adduct (19). Reduction of the disulfide with 50 mM DTT at pH 8 was quantitative. Although in this example a thiol was introduced onto the oligo-MP post-synthetically, in part to allow introduction Of $^{32}$p enzymatically at the 5' terminus, the construction of the conjugate could as easily be carried out by introduction of a thiol linker during the solid phase synthesis of the oligo-MP using, for example, 6-(tritylthio) hexyl phosphoramidite (19) commercially available from Glen Research.

In a separate reaction, 5 was combined with one equivalent each of SMCC (7) and DIPEA in anhydrous DMSO and incubated at room temperature. Combination of this reaction mixture with thiol 9 could be carried out without complete consumption of SMCC by 5 since the reactive groups present on 9, 7 and 9 combined regiospecifically. Following this scheme, 9 was completely converted to 10 when two equivalents of the neoglycopeptide 5 were used. The overall yield of the conjugate 10 was 24k (average of three syntheses), based on oligo 6.

Cellular Uptake Experiments. The cellular association of the conjugate 10 was examined, both alone and in the presence of 100 equivalents of free neoglycopeptide 5, with Hep G2 cells to demonstrate that uptake by the cells was a result of binding of the neoglycopeptide moiety of 10 to the hepatic carbohydrate receptor. As a control, an oligo-MP modified at the 5'-end with ethylenediamine (11; FIG. 2) was also incubated with Hep G2 cells under identical conditions. Modification of the 5'-phosphate with ethylenediamine was accomplished by incubation of 5'-phoshorylated 2 with 0.1 M EDAC in a buffer containing 0.1 M imidazole at pH 7 at 37° C. for 2 h followed by overnight incubation with an aqueous solution 0.3 M ethylenediamine hydrochloride buffered to pH 7.0. (Miller, P. S.; Levis, J. T., unpublished results). This modification prevents removal of the 5'-phosphate by cellular phosphatase activity.

Figure 5:
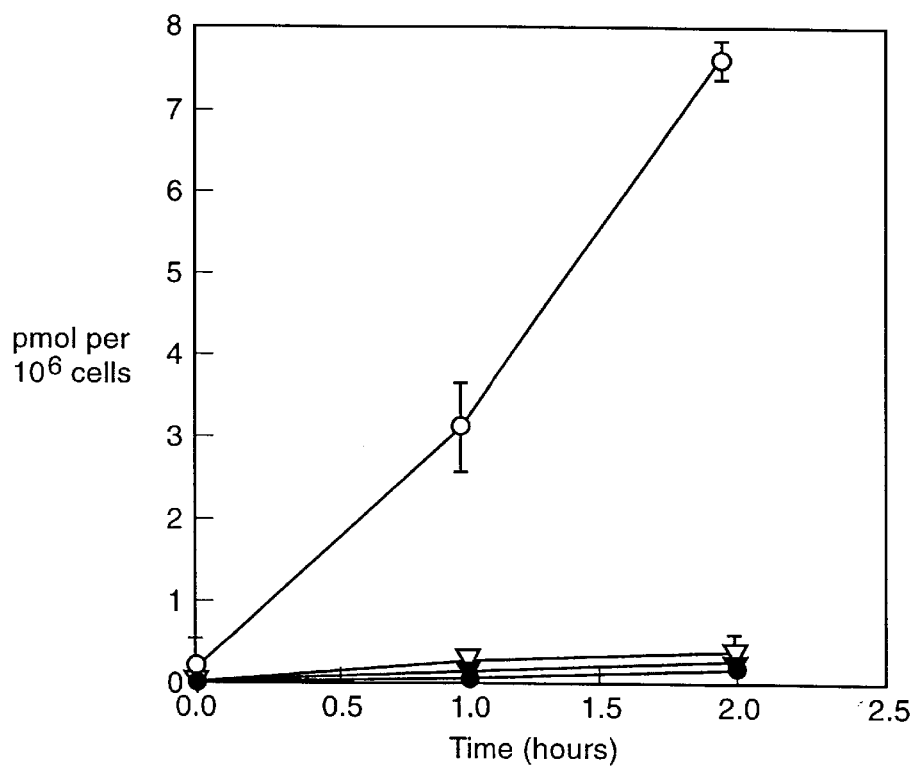
FIG. 5. Time course for the uptake by Hep G2 cells of 1 $\mu$M conjugate 10, alone (open circles) and in the presence of 100 equivalents of free 5 (closed circles), and oligo-MP 11, alone (open triangles) and in the presence of 10 equivalents of free 5 (closed triangles). Cells with incubated at 37° C. for 0, 1 and 2 hours and samples collect as described in the experimental section. Each data point represents the average of three trials ± one standard deviation.
Figure 6:
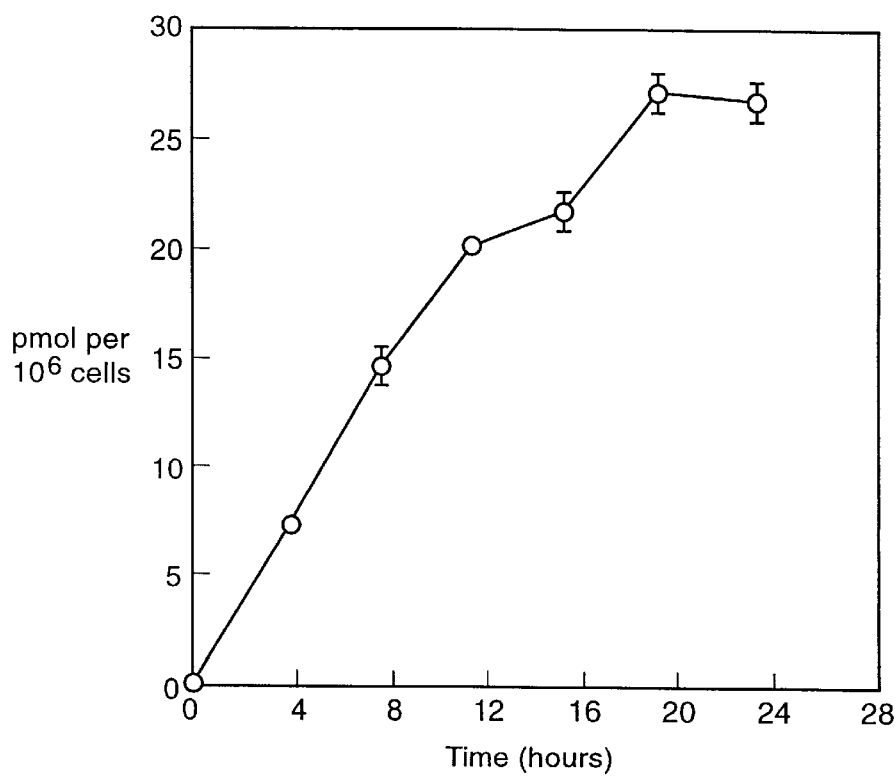
FIG. 6. 24 hour time course for the uptake of conjugate 10 by Hep G2 cells. Cells were incubated at 37° C. and the cells collected as described in the experimental section. Each data point represents the average of three experiments ± one standard deviation.

In each instance, the modified oligo-MP was present at a concentration of 1 $\mu$M in medium containing 2% fetal calf serum (FCS) and incubations were carried out at 37° C. The conjugate rapidly associated with the cells when incubated alone, loading the cells in a linear fashion to the extent of 7.8 pmol per $10^6$ cells after only two hours (FIG. 5). In contrast, when a 100-fold excess of free 5 was present with 1 $\mu$M conjugate, association of 10 was only 0.42 pmol per $10^6$ cells, a value essentially identical to that obtained with the control oligo-MP 11 (0.49 pmol per $10^6$ cells). As an additional control, Hep G2 cells were incubated with 11 in the presence of a 10-fold excess of 5 to assess the possibility that despite the absence of a covalent link between 5 and 11, 5 could cause uptake of 11 by the Hep G2 cells. The amount of cell associated 11 following a two-hour incubation was only 0.60 pmol per $10^6$ cells, significantly less than found with the conjugate 10. In addition, the uptake of 10 by Hep G2 cells for longer times was examined (1 $\mu$M conjugate, 37° C.), and found to be linear up to ca. 24 hours reaching a value of 26.6 pmol per $10^6$ cells (FIG. 6). The results of these experiments indicate that: (1) the conjugate 10 associates with Hep G2 cells by binding specifically to the asialoglycoprotein receptor; (2) a covalent link between the oligo-MP and neoglycopeptide is essential for significant enhancement of the association of the oligo-MP with Hep G2 cells; and (3) uptake of 10 by Hep G2 cells does not appear to saturate up to 24 hours under the conditions used in this study.

Figure 7:
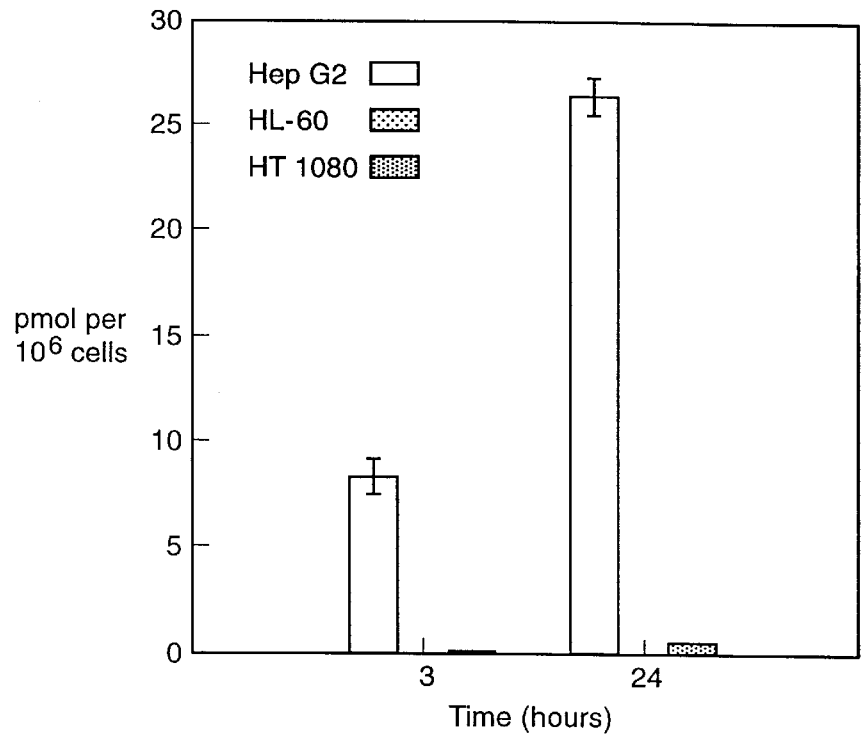
FIG. 7. Tissue specific uptake of conjugate 10 by Hep G2, HL-60 and HT 1080 cells. Cells were collected and the amount of [$^{32}$p] determined at 3 and 24 h for each cell line. Experiments were done in triplicate and the data expressed as the average ± one standard deviation.

Cell-type specificity of the compounds was also examined. It is well established that the asialoglycoprotein receptor is found on the surface of hepatocytes and represents an efficient means for selectively targeting this tissue for delivery of a variety of therapeutic agents (21). Tissue specificity was examined by incubating three human cell lines, Hep G2, HL-60 and HT 1080, in medium containing 1 $\mu$M conjugate 10 and 2% FCS at 37° C. for 3 and 24 hours. The only cell line to exhibit significant uptake of 10 was Hep G2. After incubation for 3 and 24 hours, 8.5 and 26.7 pmol per $10^6$ cells, respectively, was associated with the cells (FIG. 7). In contrast, after 24 h only 0.10 and 0.53 pmol per $10^6$ cells were associated with the HL-60 cells and HT 1080 cells, respectively. This result is consistent with previous findings which showed the conjugate YEE(ah-GalNAc)$_3$-HSA-poly-L-lysine to deliver DNA primarily to the liver of mice (16).

The cellular association and cell-type specificity of a novel oligo-MP neoglycopeptide conjugate, [YEE(ah-GalNAc)$_3$]-SMCC-AET-pU$^m$pT$_7$ (10), was examined using three human cell lines. The cellular association of 10 by Hep G2 cells is remarkably efficient and linear up to 24 hours reaching maximum level of 26 pmol per $10^6$ cells. Using an approximation that $10^6$ cells represents a volume of 1 $\mu$L, then the intracellular concentration of this conjugate can be as high as 26 $\mu$M. In addition, little conjugate associates with HL-60 or HT 1080 cells, demonstrating that the neoglycopeptide 5 is capable of delivering the oligo-MP 6 in a highly selective manner to hepatocytes.

Whole animal biodistribution and pharmacokinetics

Synthesis of [YEE(ah-GalNAc)$_3$]-SMCC-AET-[$^{32}$p] pU$^m$pT$_7$ (10) and [YEE(ah)$_3$]-SMCC-AET-[$^{32}$p]-pU$^m$pT$_7$ (12).

Briefly, the parent oligodeoxynucleoside methylphosphonate (oligo-MP), U$^m$pT$_7$, was 5' end-labeled with [$\gamma$-$^{32}$p]-ATP and ATP to give pU$_m$pT$_7$ having a specific activity of 300 $\mu$Ci/14 nmol (the * indicates the position of the radioactive nuclide). The 5' phosphate was modified with cystamine in the presence of 1-methylimidazole and water soluble carbodiimide. The resulting disulfide was reduced with excess dithiothreitol and conjugated with the ligand, YEE(ah-GalNAc)$_3$, using the heterobifunctional cross-linking reagent SMCC. The conjugate (1) was purified by polyacrylamide gel electrophoresis, extracted from the gel and desalted using a SepPak cartridge. The pure conjugate was characterized both enzymatically and chemically. A portion of the conjugate was treated with N-acetylglucosamidase in order to completely remove the GalNAc residues (12). Both 10 and 12 were >99% pure as judged by PAGE analysis. The solutions containing the conjugates were placed in sterile test tubes and lyophilized under aseptic conditions in preparation for the whole animal biodistribution and pharmacokinetic experiments.

Figure 8A:
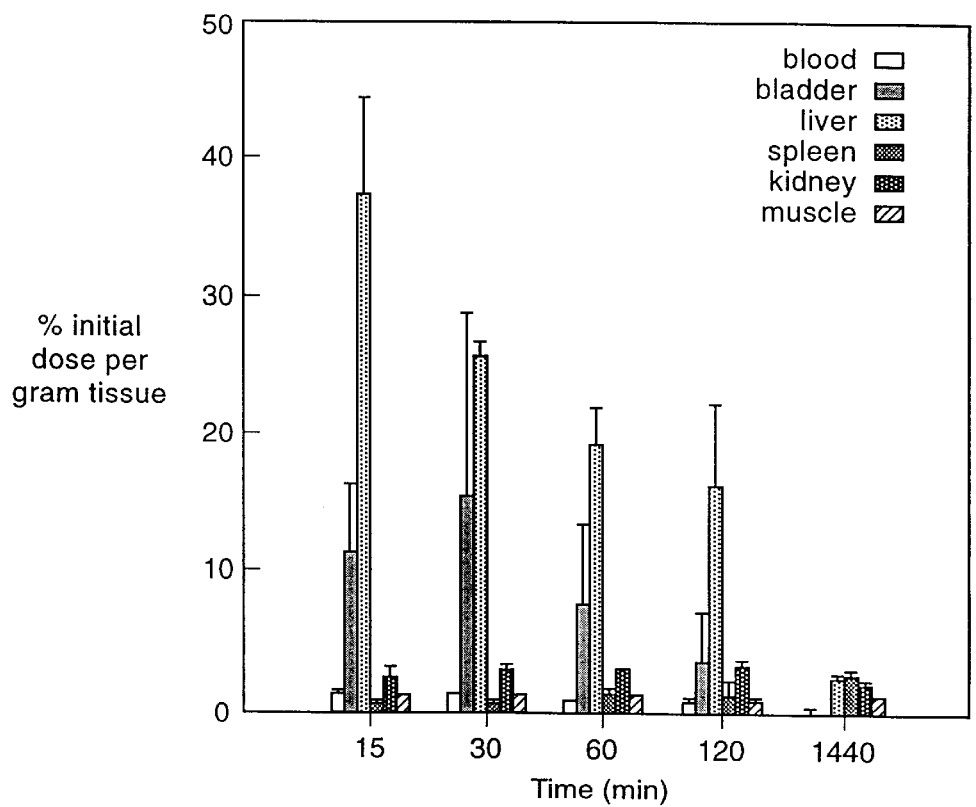
FIG. 8. Tissue Distribution of conjugate 10 and conjugate 12, which was produced by removing the terminal GalNAc residues of conjugate 10 with N acetylglucosamidase. Panel A: Percent initial dose per gram tissue versus time post-injection for conjugate 10. Panel B: Percent initial dose per gram tissue versus time post-injection for conjugate 12.
Figure 8B:
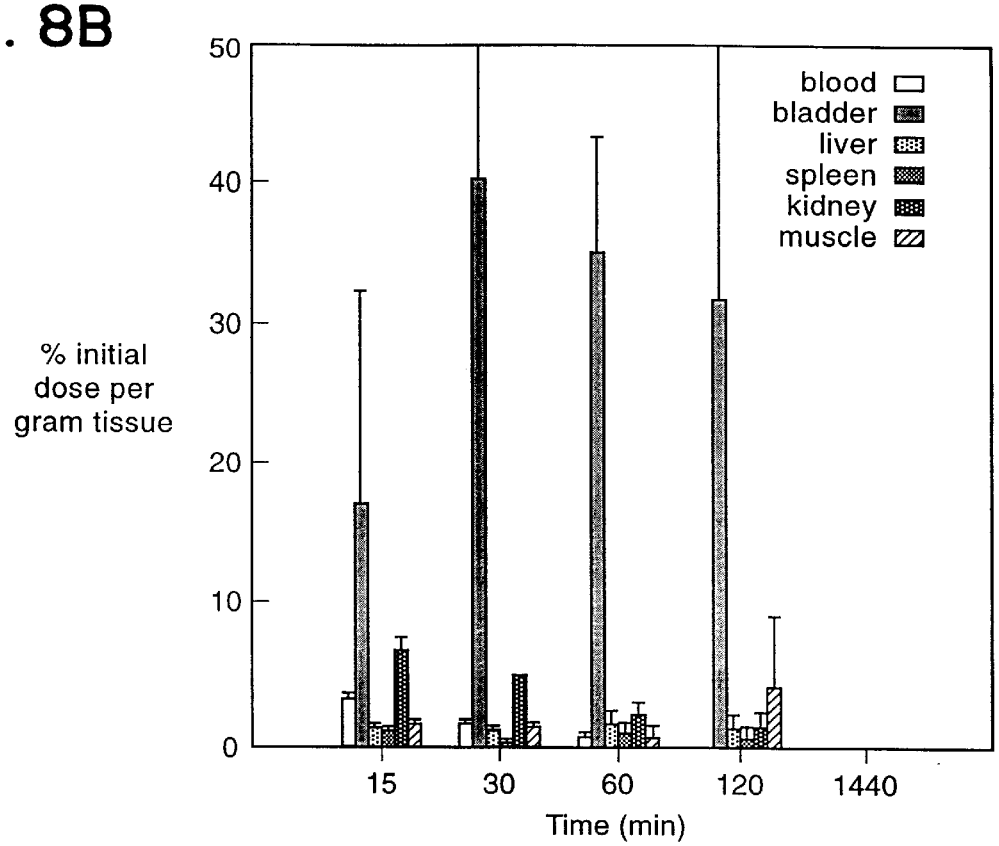

Whole animal biodistribution and pharmacokinetics. The conjugates 10 and 12 were redissolved in sterile water. Each mouse received 0.11 $\mu$Ci (7 pmol) of conjugate 10 and 0.036 $\mu$Ci (1.2 pmol) of 12 by tail vein injection. Sequential blood, bladder/urine and tissue samples (liver, spleen, kidney and muscle) were collected at 15, 30, 60, 120 and 1440 min post-injection. Three mice were used for each time point for a total of 30 mice. The mouse was killed by cervical dislocation at the time of sampling. Whole wet tissue was weighed in a scintillation vial and digested at 50° C. with NCS solubilizer. The samples were decolorized, dissolved in scintillation cocktail and the levels of radioactivity determined by scintillation counting. The raw data was converted into percent initial dose per gram of tissue, except for that obtained from the bladder, which was expressed as percent initial dose per tissue sample owing to the difficulty of obtaining these tissues intact (see FIG. 8).

At the 15 min time point, 37% of the initial dose per gram of tissue of conjugate 10 was associated with the liver whereas lesser amounts, 11% and 2.4%, respectively, were associated with the bladder/urine and kidney. When it is considered that the liver on average has a mass of 1.4 g, then ca. 52% of the initial dose was associated with the liver after 15 min post-injection. The other tissues examined contained <1.2% of the initial dose after 15 min. The amount of liver associated radioactivity steadily decreased at longer times, eventually reaching a level of 2.3% after 24 hours. In contrast, the amount of conjugate increased in the bladder and urine between 15 and 30 min, and then decreased to similar levels.

Conjugate 12, which lacks the three GalNAc residues, rapidly associated with the bladder/urine and, to a lesser extent, the kidney, and showed no specificity for the liver. For example, at 30 min the percent of initial dose per gram of tissue was 40%, 5.0% and 1.1% for the bladder/urine, kidney and liver, respectively.

It is apparent from these data that: (1) conjugate 10 associates specifically with the liver; (2) association of conjugate 10 is wholly dependent upon the presence of the GalNAc residues on the ligand; (3) conjugate 10 or, more likely, its metabolites, are cleared from the liver within 24 hours and eliminated from the mouse via the kidney and, hence, finds its way into the bladder and urine. Furthermore, owing to the low level of radioactivity found in the blood versus the large amount of radioactivity associated with the liver, it can be concluded that conjugate 10 is delivered into the hepatocytes rather than simply associated with the liver within the interstitial space.

Synthetic Procedures for Compounds 1b and 1c

Additional examples of compounds of the invention are shown in Table 5.

TABLE 5

Oligonucleotide Alternating Methylphosphonate Analogs

Sequence 1 (n = 7)  ApGpUpCpApGpUpCpApGpUpCpApGpU
2 (n = 7)  GpUpUpCpUpCpCpApUpGpUpUpCpApG
3 (n = 10) UpUpApUpApApGpGpUpCpGpApUpGpUpCpCpApU where
p: phosphodiester linkage
p: methylphosphonate linkage
ps: phosphorothioate linkage TABLE 5-continued Oligonucleotide Alternating Methylphosphonate Analogs

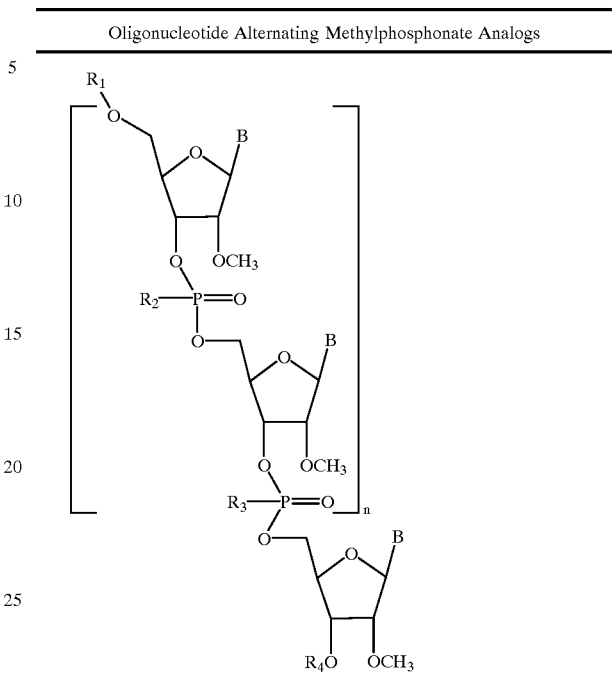

Figure 3:
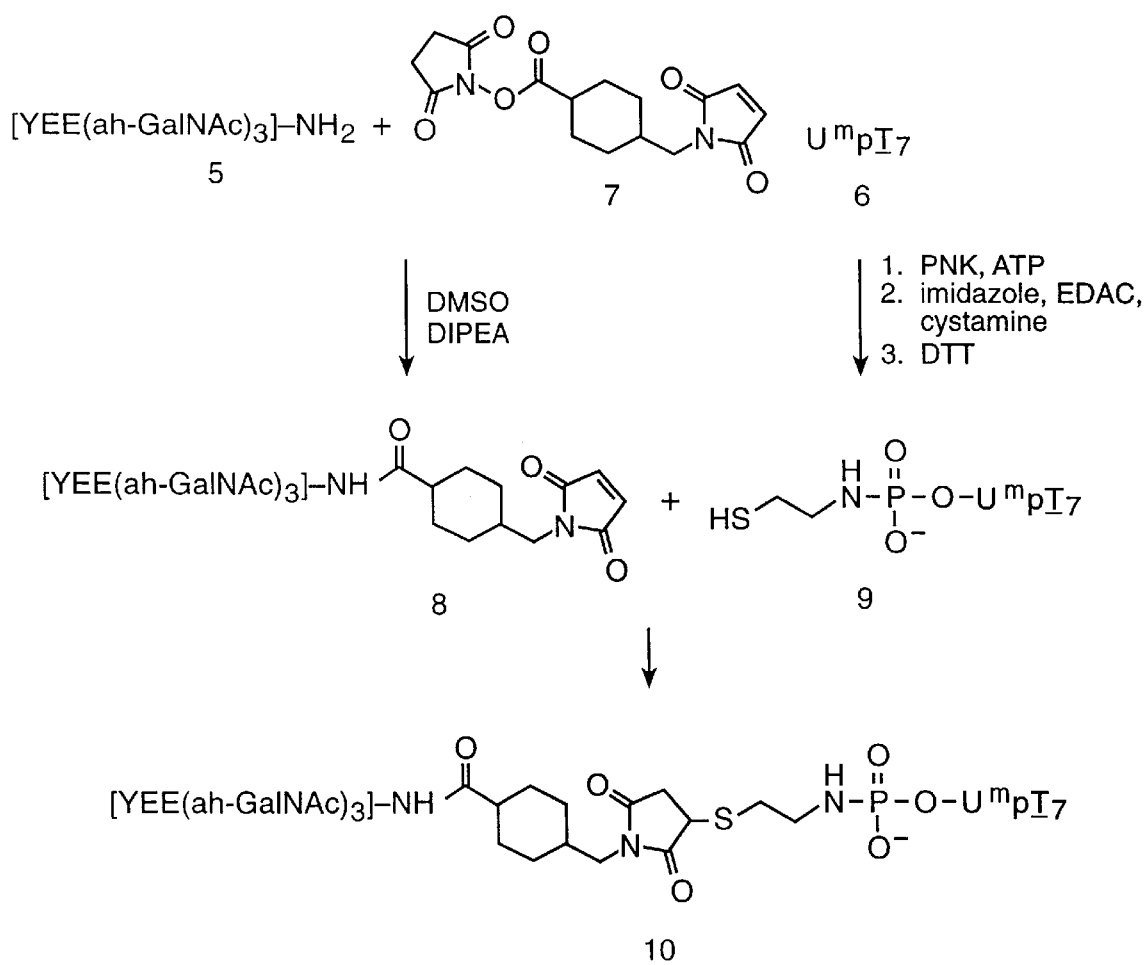
FIG. 3. Reaction scheme for the synthesis of [YEE(ah-GalNAc)$_3$]-SMCC-AET-pU$^m$pT$_7$ (10).
Figure 4:
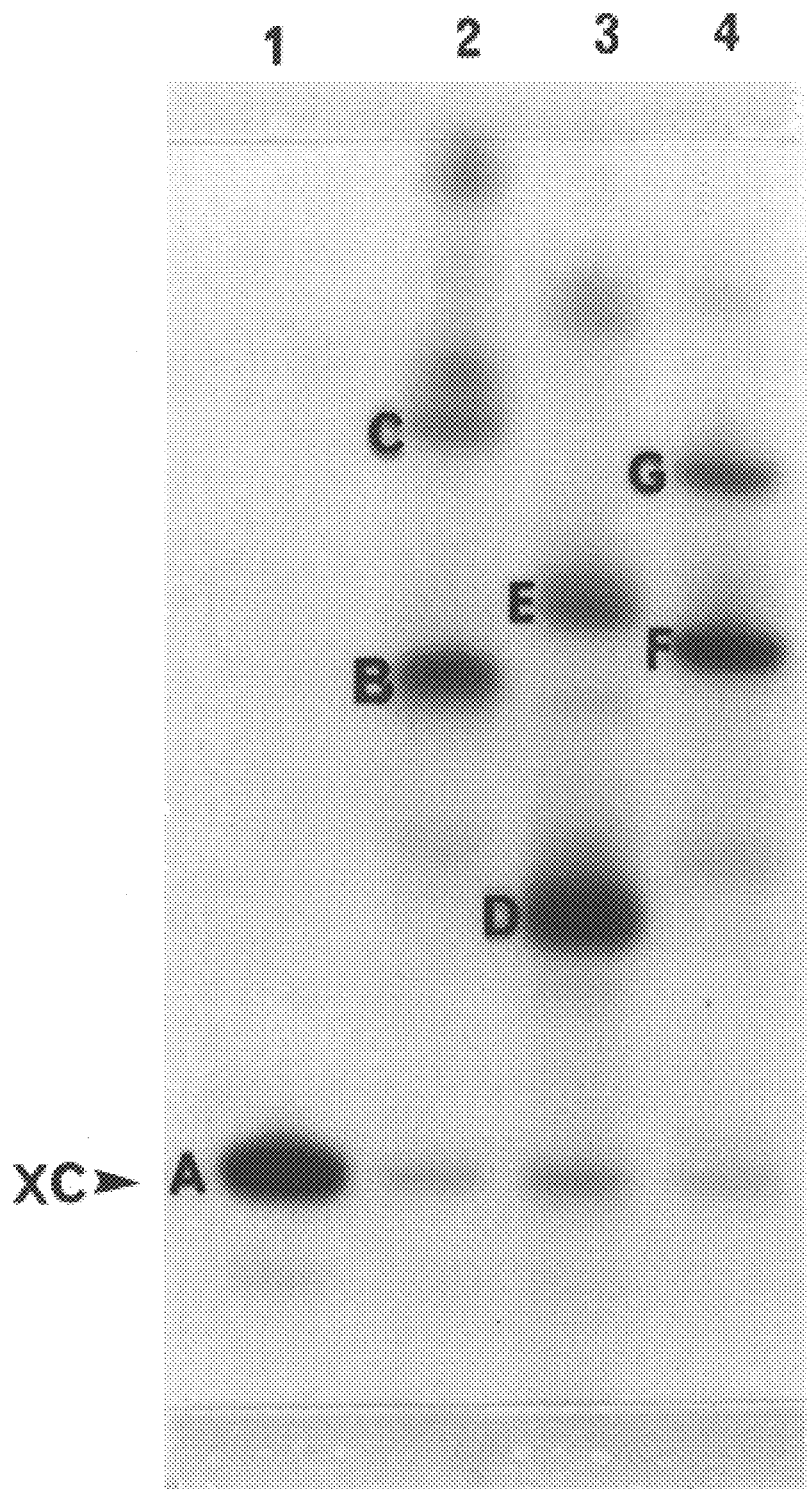
FIG. 4. PAGE analysis (15% polyacrylamide, 4 V/cm, 2 h) of intermediates in the synthesis of conjugate 10. Lane 1, [5'-$^{32}$P]-labeled 6 (band A). Lane 2, [5'-$^{32}$P]-cystamine adduct (band B) and corresponding thymidine-EDAC adducts (bands C). Lane 3, [5'-$^{32}$P]-thiol 5 (band D) and corresponding thymidine-EDAC adducts (bands E). Lane 4, [5'-$^{32}$P]-conjugate 10 (band F) and corresponding thymidine-EDAC adducts (bands G).
Figure 9:
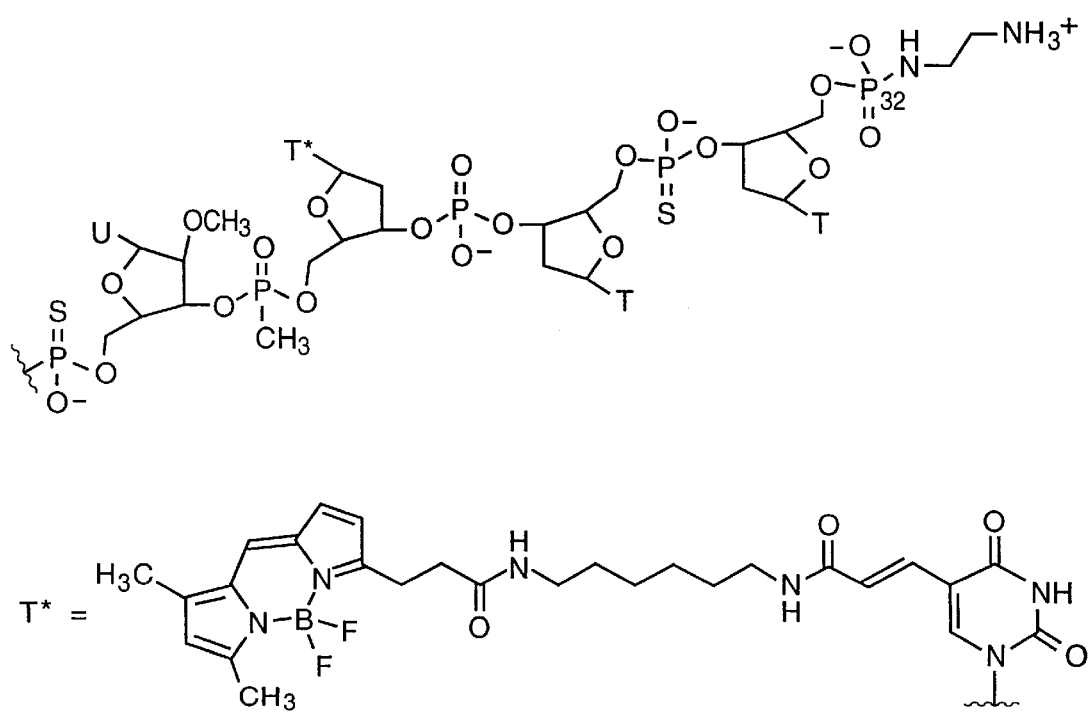
FIG. 9. Structure of the Tracer, 3' conjugate.
Figure 11:
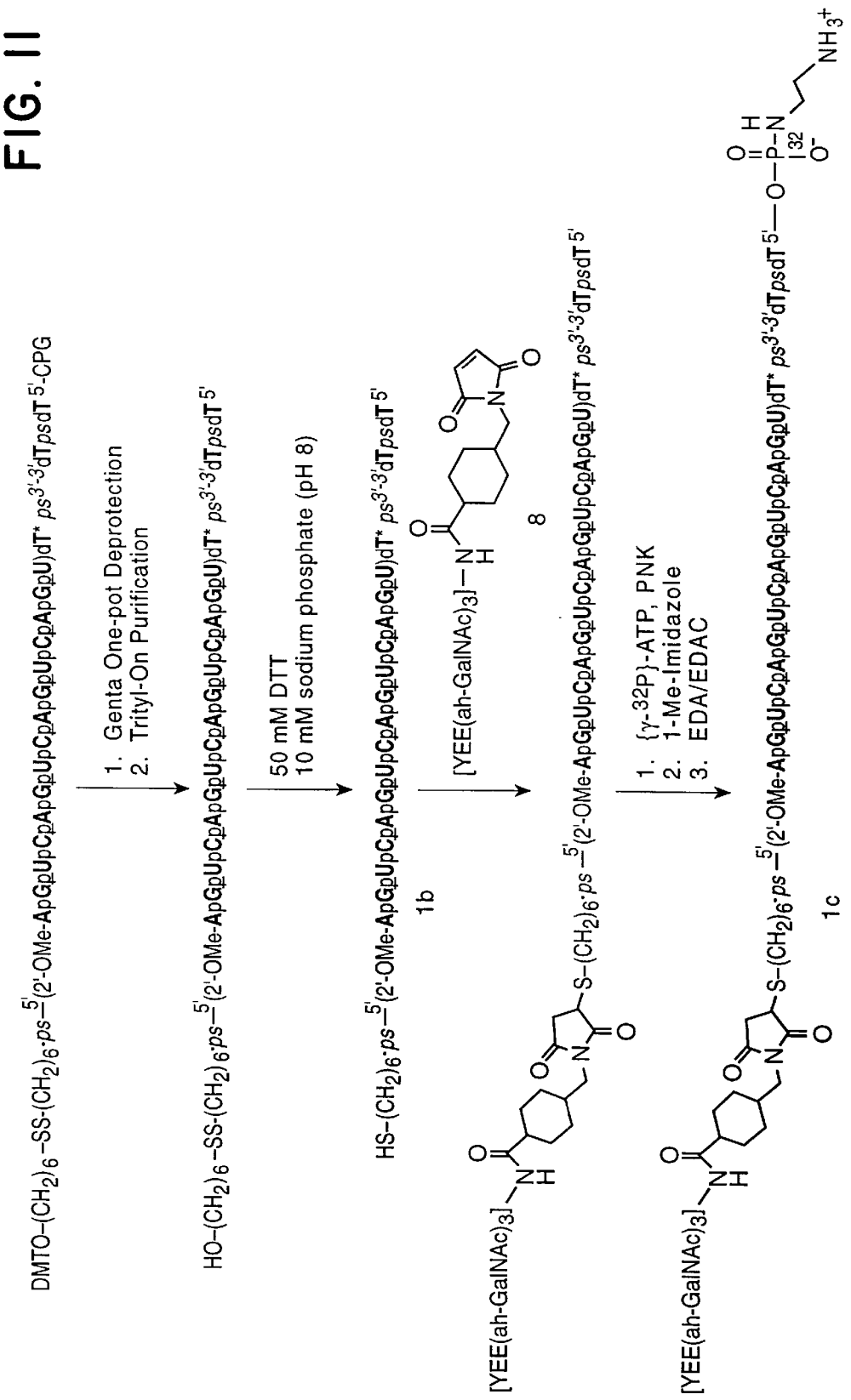
FIG. 11. Reaction scheme for the synthesis of 1c.

| Oligonucleotide | $R_1$ | $R_2$ | $R_3$ | $R_4$ |
|---|---|---|---|---|
| a | H | O$^-$ | $CH_3$ | 3'-conjugate |
| b | C6-thiol-ps | O$^-$ | $CH_3$ | 3'-conjugate |
| c | 5'-conjugate | O$^-$ | $CH_3$ | 3'-conjugate |
| d | Ligand-SMCC-AET | O$^-$ | $CH_3$ | H |
| e | EDA | O$^-$ | $CH_3$ | H | where
Ligand: YEE(ah-GalNAc)$_3$
5'-conjugate: YEE(ah-GalNAc)$_3$-SMCC-S(CH$_2$)$_6$-ps linkage (FIG. 3)
3'-conjugate: Tracer Unit (FIG. 9)
EDA: ethylenediamine Sequences 1–3 can be linked with substituent groups indicated as oligonucleotides a-e at the bottom of Table 5 using the synthesis methods described hereinbelow to form further examples of compounds of the invention. For example, 1b consists of sequence 1 with substituents according to the invention of C6thiol-ps, O$^-$, CH$_3$, and 3'-conjugate (the structure of which is shown in FIG. 9). Compounds of the structures indicated by 1b (compound 13) and 1c (compound 14) were synthesized according to the scheme shown in FIG. 3, as set forth in detail in Examples 8 and 9. It will be clear that with suitable substitution in starting material and changes in the synthesis the other combinations can be similarly synthesized.

EXAMPLE 7

Synthesis of SMCC-YEE(ah-GalNAc)$_3$ (8) (Alternative method).

About 1–2 μmole of YEE(ah-GalNAc)$_3$ was dried into a 1 mL glass Reacti-vial. To this solution, anhydrous DMSO (250 μL) and anhydrous DIPEA (3 μL) was added, then treated with 150 μL of a solution containing vacuum-dried SMCC (6 mg) in anhydrous DMSO. The mixture was vortexed briefly and left stand at room temperature for 2 hours. Analysis by reversed-phase hplc indicated complete conversion of the starting YEE(ah-GalNAc)$_3$ (elution time: 7.3 min) to the desired product SMCC-YEE(ah-GalNAc)$_3$ (elution time: 9.8 min). The reaction mixture was then diluted to 10 mL with 50 mM sodium phosphate (pH 5.8) containing 2% $CH_3CN$ and was loaded onto a Sep-Pak cartridge. The cartridge was washed with 10 mL of 50 mM sodium phosphate (pH 5.8) containing 2% $CH_3CN$ and the product was eluted with 10 mL of 25% $CH_3CN/H_2O$. The product was concentrated under reduced pressure in a Speed-vac and was further purified on a semi-preparative reversed-phase C18 column. Fractions containing pure SMCC-YEE(ahGalNAc)$_3$ were pooled and desalted on a Sep-Pak. Final yield of product: $1.89°D_{276}$ or 1.35 μmole.

EXAMPLE 8

Preparation of Thiol-modified Oligonucleotides [(e.g. compound 1b in Table 5).

Novel types of oligomers, a random (Table 5, sequence 1), anti-HBV (Table 5, sequence 2) and core (Table 5, sequence 3) which contain 2'-O-methylribose with alternating phosphodiester and methylphosphonate internucleotide linkages were used in this study. A 5'-disulfide linker which can be reduced to generate a thiol group for conjugation with the neoglycopeptide was introduced via a phosphoramidite synthon. Finally, an oligonucleotide tracer unit in the form of a 3'-conjugate was used so that phosphorylatable 3'-end could be used to introduce the radioactive $^{32}p$ label were also employed in this study. These modified oligomers were synthesized on a solid-phase DNA synthesizer, using corresponding phosphoramidites and methylphosphonamidites from a commercial source (Glen Research). The tracer was synthesized (FIG. 10) using dT-5'-Lcaa-CPG as the solid phase and dT-5'-CE phosphoramidite, 5'-DMT-5-[N(trifluoroacetyl)hexyl-3-acrylimide]-2'-deoxyuridin e, 3'-[(2cyanoethyl)-(N,N'-diisopropyl)]phosphoramidite and were commercially available from Glen Research. The 5'-disulfide linker was introduced into these oligomers by coupling a C6-disulfide cyanoethyl-phosphoramidite synthon (Glen Research) at the final coupling step of the solid-phase synthesis. When necessary, the Beaucage reagent (Glen Research) was substituted for the low moisture oxidizer to effect sulfurization of the phosphite to give the phosphorothioate according to standard established procedures. The oligomers were deprotected under Genta one-pot method and were purified by trityl-on procedures. Final purification were conducted using a preparative reversed-phase C18 column.

The reduction of the disulfide moiety to the thiol was effected by the treatment of the 5'-disulfide-containing oligomers with DTT. Thus, a $2.5OD_{260}$ (~16 nmole) disulfide oligomer was dissolved in 400 μL of freshly prepared and degassed 50 mM DTT solution in 10 mM sodium phosphate, pH 8. The mixture was incubated at 37° C. for 2 hr. Quantitative reduction were confirmed by reversed-phase HPLC analysis, which shows that the thiol oligomers elute faster than the parent disulfide oligomers. The thiol oligomer was then purified on a Sephadex G-25 column (10×300 mm) to remove DTT and salts. Column packing and sample elution were effected by the use of degassed 20% ethanol-water. The G-25 fraction containing the pure thiol oligomer was used immediately in the next reaction to minimize unwanted oxidation.

EXAMPLE 9

Synthesis of SMCC-YEE(ah-GalNAc)$_3$-containing Oligonucleotides (compound 14, shown as 1c in Table 5).

The G-25 fraction containing $1.8OD_{260}$ (12 nmole) pure thiol oligomer (1b) was mixed with SMCC-YEE(ah-GalNAc)$_3$ (50 nmole) immediately after it was collected. The mixture was concentrated to dryness in a speed-vac. The residue was dissolved in 100 μl of degassed 50% $CH_3CN$ containing 0.1 M sodium phosphate, pH 7. The solution was further degassed in a speed-vac by applying vacuum for about 5 min. The solution was then capped tight and incubated at room temperature overnight to allow conjugation to complete. To determine the yield of conjugation, a 0.5 μL portion of the reaction was phosphorylated using [τ-$^{32}P$]-ATP and PNK and analyzed by 20% denaturing PAGE. This result indicated quantitative conjugation of the thiol oligomer with the neoglycopeptide. The conjugate was confirmed by its significant gel mobility shift upon chymotrypsin digestion and its inability to shift upon DTT treatment. The conjugate was finally purified by a Sephadex G25 column, eluting with 20% ethanol and then used in further studies.

EXAMPLE 10

CELLULAR UPTAKE EXPERIMENTS ON Hep G2 2.2.15

Hep G2 2.2.15, a human hepatocellular carcinoma cell line stably transfected with human hepatitis B virus DNA (22), was a gift of Dr. G. Y. Wu. Other lines of suitable cells are known to persons of skill in the art, for example PLC/PRF/5 (Alexander cells), a human hepatoma secreting hepatitis B surface antigen, has been described (23) and is available from the American Type Culture Collection.

Hep G2 2.2.15 cells were maintained in 1× Dulbecco's Modified Eagles Medium supplemented with 10% fetal calf serum. All other materials used were identical to those cited in the Cellular Uptake section above.

HepG2 2.2.15 cells were inoculated into 2 cm$^2$ wells and grown in 1× DMEM containing 10% FCS to a density of $10^5$ cells per well. The maintenance media was aspirated and the cells were incubated at 37° C. with 0.5 ml DMEM containing 2% FCS and made 1 uM in [5'-$^{32}p$] with 1c, 1d, or le. All other methods were identical to those followed in Example 4.

In order to measure the efflux of 1c, HepG2 2.2.15 cells were seeded and incubated with 1 uM of the conjugated oligomer for twenty-four hours as described above. The oligomer containing medium was then aspirated and the cells washed twice and subsequently incubated in 0.5 ml maintenance medium. At designated times the cells were collected and lysed as described in the Cellular Uptake section of the Provisional Application. Efflux was determined by monitoring the amount of radioactivity and by inference the concentration of the conjugated oligomer in the cell lysate.

DISCUSSION

The cellular uptake experiments described hereinabove were extended to examine the cellular association of 1d with Hep 2G 2.2.15 cells. As in the case of the oligo-mp, a control was prepared by modifying the $^{32}p$ labeled 5' end of 1 with ethylenediamine to yield le.

The results of this experiment were very similar to those performed with the modified oligo-mp. The conjugated 2'OMe alternating oligomer (1d) was taken up by Hep2G 2.2.15 cells in a linear fashion to the extent of 7.7 pmoles/10% cells after two hours incubation (Table 6).Uptake increased to 14.2 pmoles/$10^6$ cells in three hours and peaked at 28.5 pmoles/106 cells after twenty-four hours incubation. In contrast, the EDA modified oligomer (1e) associated with Hep G2 2.2.15 cells to the extent of 0.275 pmoles/$10^6$ cells after two hours, 0.978 pmoles/$10^6$ cells after three hours and 0.385 pmoles/$10^6$ cells after twenty-four hours incubation (Table 6).

A further modification was made to 1d by adding a phosphorothioate protected [$^{32}$p] labeled tracer to the 3' end to yield 1c. The uptake of this conjugated oligomer (1c) was very similar to that displayed by id. Cellular association occurred in a linear fashion up to 18.6 pmoles/$10^6$ after twelve hours incubation and reached a peak value of 28.97 pmoles/$10^6$ cells after twenty-four hours incubation (Table 7).

Subsequently, the exit rate of the cell associated 1c was also assessed. The concentration of the conjugated 2'OMe alternating oligomer in Hep G2 2.2.15 cells displayed a steady decline to a value of 12.45 pmoles/$10^6$ cells twenty-four hours after the treatment was removed (Table 8).

The above experiments demonstrate that neoglycopeptide 5 is capable of delivering a biostable oligomer consisting of all 2'-O-methylribose nucleosides and alternating methyl phosphonate, phosphodiester internucleotide linkages to hepatocytes in a highly efficient manner. In addition, the placement of a phosphorothioate protected tracer at the 3' end of the conjugated oligomer (1c), has no significant impact on cellular uptake. Furthermore, these studies also show that the internalized oligomer exits the cell reaching a value that is 58% of the peak uptake twenty-four hours after treatment was terminated.

TABLE 6

Uptake of conjugated YEE(ah-GAlNac)$_3$-SMCC-AET-2'0-Me
5'AG$_p$UC$_p$AG$_p$UC$_p$AG$_p$UC$_p$AG$_p$U$^{3'}$
(1d) and EDA-2'-0-Me-
5'AG$_p$UC$_p$AG$_p$UC$_p$AG$_p$UC$_p$AG$_p$U$^{3'}$
(1e) by Hep 2G 2.2.15 cells in
culture (pmoles/$10^6$ cells)

| OLIGOMER | 1 HOUR | 2 HOURS | 3 HOURS | 24 HOURS |
|---|---|---|---|---|
| 1d | 3.63 | 7.71 | 14.16 | 28.52 |
| 1e | 0.277 | 0.305 | 0.400 | 0.450 |

TABLE 7

Uptake of YEE(ah-GAlNac)$_3$-SMCC—S(CH$_2$)$_6$-ps-2'0-Me-
5'AG$_p$UC$_p$AG$_p$UC$_p$AG$_p$UC$_p$AG$_p$U$^{3'}$
-U$^M$dT*$^{3'-3'}$ (dT-T)-$^{32}$P-EDA
(1c) by Hep G2 2.2.15 cells in culture (pmoles/$10^6$ cells)

| OLIGOMER | 4 HOURS | 8 HOURS | 12 HOURS | 16 HOURS | 24 HOURS |
|---|---|---|---|---|---|
| 1c | 9.44 | 18.60 | 22.05 | 24.92 | 28.97 |

TABLE 8

Efflux of YEE(ah-GAlNac)$_3$-SMCC—S(CH$_2$)$_6$-ps-2'0-Me-
5'AG$_p$UC$_p$AG$_p$UC$_p$AG$_p$UC$_p$AG$_p$U$^{3'}$
-U$^M$dT*$^{3'-3'}$ (dT-T)-$^{32}$P-EDA
(1c) by Hep G2 2.2.15 cells in culture (pmoles/$10^6$ cells)

| OLIGOMER | 4 HOURS | 8 HOURS | 12 HOURS | 16 HOURS | 24 HOURS |
|---|---|---|---|---|---|
| 1c | 25.88 | 23.96 | 20.23 | 16.04 | 12.45 |

EXAMPLE 11

Whole animal experiments were performed to test for the ability of a delivery vehicle of the invention, i.e, which contains the asialoglycoprotein ligand, YEE(ah-GalNAc)$_3$ radiolabeled with $^{32}$P, to deliver synthetic oligo-MPs specifically to the liver of mice and to examine the metabolic fate of this conjugate in isolated Hep G2 cells and in vivo in mouse liver and urine.

For comparison, a conjugate which lacks the three terminal Gal NAc residues, was also synthesized. This sugarless conjugate served as a control for the study of ligand (GalNAc)-specific uptake in mice.

Material and Methods

EXAMPLE 12

Tissue Distribution and Time Course of Clearance.

Male CD-1 mice (Charles River), weighing 22 to 35 g, received a single injection via tail vein of 7–30 picomoles of [$^{32}$P]-[YEE(ah-GalNAc)$_3$]-SMCC-AETpU$^m$pT$_7$ (10) or 7 pmole of [$^{32}$p]-[YEE(ah)$_3$]SMCC-AET-pU$^m$pT$_7$ (12) contained in 0.2 mL of saline. The mice were sacrificed by cervical dislocation at 15, 30 and 60 minutes and 2, 4, 6 and 24 hours. Blood, liver, kidneys, spleen, muscle, upper and lower gastrointestinal tract and feces were collected and weighed. Representative samples from these organs and tissues were weighed and placed in glass vials. In order to collect the urine (2 hours post injection), the external urethra of the mice was ligated under short ether anesthesia and, after sacrifice, the bladders were removed and placed into glass vials. SOLVABLES® (NEN (consisting of 3% N,N'-dimethyl lauryl amine oxide, 3% alkyloxypolyethyleneoxyehtanol and 2% sodium hydroxide in an aqueous solution); 1 mL) was added to each sample. The samples were then placed on a slide warmer to be digested overnight and removed the next morning to cool. The digested samples were decolorized with 3 to 7 drops of H$_2$O$_2$ (30% w/v), and 10 mL Formula 989 (NEN) scintillation cocktail were added. The amount of radioactivity was determined by scintillation counting (Packard 1900 TR; <3% error). Aliquots of the injected dose were counted along with the samples to calculate the percent dose per organ or gram tissue.

EXAMPLE 13

Analysis of metabolites isolated from Hep G2 Cells.

Cells (ca. $_{10}{}^5$) were incubated in media containing 1 μM [$^{32}$P]-labeled 1 for 2, 4, 8, 16 and 24 h, washed with PBS (2×), pelleted through silicon oil and lysed (0.5% NP 40, 100 mM sodium chloride, 14 mM Tris-HCl pH 7.5, 30% ACN). The lysate was extracted with 50% aqueous acetonitrile (v/v) twice. The extracts were lyophilized, redissolved in formamide loading buffer and analyzed by PAGE (15%, 2 V/cm, 30 min).

EXAMPLE 14

Analysis of Conjugate Metabolism.

Male CD-1 mice, weighing between 22 to 35 g, received a single injection via tail vein of 40 pmole of [$^{32}$P]-[YEE (ah-GalNAc)$_3$]SMCC-AET-pU$^m$pT$_7$ (10). Animals were sacrificed after 15, 60 and 120 minutes. Livers and bladders were collected as before, placed into plastic vials and immediately frozen (80° C.). Samples of liver were thawed to 0° C. and weighed (average mass 0.25 g). The tissue was homogenized (Polytron PCU-2-110 Tissue Homogenizer) in 4 volumes of acetonitrile/water (1:1). Tissue debris was removed by centrifugation (10,000 g, 20 min, 0° C.; Sorval Model RC-5B Refrigerated Superspeed Centrifuge). The supernatent was removed and the extraction procedure repeated. Typical recovery of radioactivity from the liver samples was ³90% as judged by comparison of aliquots of decolorized homogenate and supernatant. A portion of the supernatent was filtered through a Centricon filter (30,000 MWC; 20 min, 0° C., 10,000 g; Herml Z 360 K Refrigerated Microcentrifuge) and lyophilized. The residue was redissolved in 10 mL formamide loading buffer (90% formamide, 10% 1× TBE, 0.2% bromophenol blue, and 0.2% xylene blue) in preparation for analysis by polyacrylamide gel electrophoresis (PAGE; 15%, 20×20×0.75 cm, 2 V/cm, 45 min). The urine was collected from the bladder, which had been thawed to 0° C., and was deproteinized with ethanol (1:2 v/v) at 0° C. for 30 min. The precipitated proteins were removed by centrifugation (16,000 g, 20 min, 0° C.). Recovery of radioactivity was estimated to be ³90% by comparing the aliquots of the supernatent and the protein pellet. A portion of the supernatent was lyophilized, redissolved in formamide loading buffer and analyzed by PAGE (15%, 20×20×0.75 cm, 2 V/cm, 45 min). Standards were produced by incubation of full-length conjugate (10) with, in separate reactions, N-acetylglucosamidase in 50 mM sodium citrate, pH 5.0, chymotrypsin in 10 mM Tris·HCl containing 200 mM KCl, pH 8.0 and 0.1 N HCl each at 37° C. for 30 min.

EXAMPLE 15

Tissue Distribution and Kinetics of Liver Uptake and Clearance.

In order to investigate the in vivo tissue and organ distribution of conjugate 10, mice were injected via tail vein with radiolabeled conjugate as described above and the amount of radioactivity associated with each organ determined by scintillation counting. Table 9 shows the conjugate associates to the greatest extent with the liver, reaching a value of 69.9% of the injected dose 15 minutes post-injection. The ranking of total radioactivity in the other tissues measured at 15 minutes post-injection was, in decreasing order: muscle>kidney>blood>spleen. The peak value of radioactivity for the urine was 28% of the injected dose and was reached after 30 minutes. The amount of radioactivity associated with the kidneys and blood decreased over time. It is noteworthy that, while it may be expected that metabolites of the conjugate produced in the liver would become deposited in the gastrointestinal tract via bile excretion, little radioactivity was associated with the gall bladder, upper and lower gastrointestinal tract, and feces (Table 9).

Table 11 shows that conjugate 12, which lacks the three terminal GalNAc residues, was distributed in the order: muscle>blood>kidneys>liver >spleen. The amount of muscle and liver radioactivity appeared to remain constant whereas that associated with the blood and kidneys decreased over the 24 hour study. The peak value of radioactivity in the urine was 39.9% at 30 minutes post-injection. As a control, an identical experiment was carried out with conjugate 10 (Table 11). The ranking of tissue distribution was, in order of decreasing amounts of radioactivity: liver>>muscle>kidney>blood>spleen. The urine contained, after 30 minutes post-injection, 17% of the injected dose.

EXAMPLE 16

Polyacrylamide Gel Electrophoresis Analysis of the Metabolism of Conjugate 10.

Figures 12A, 12B:
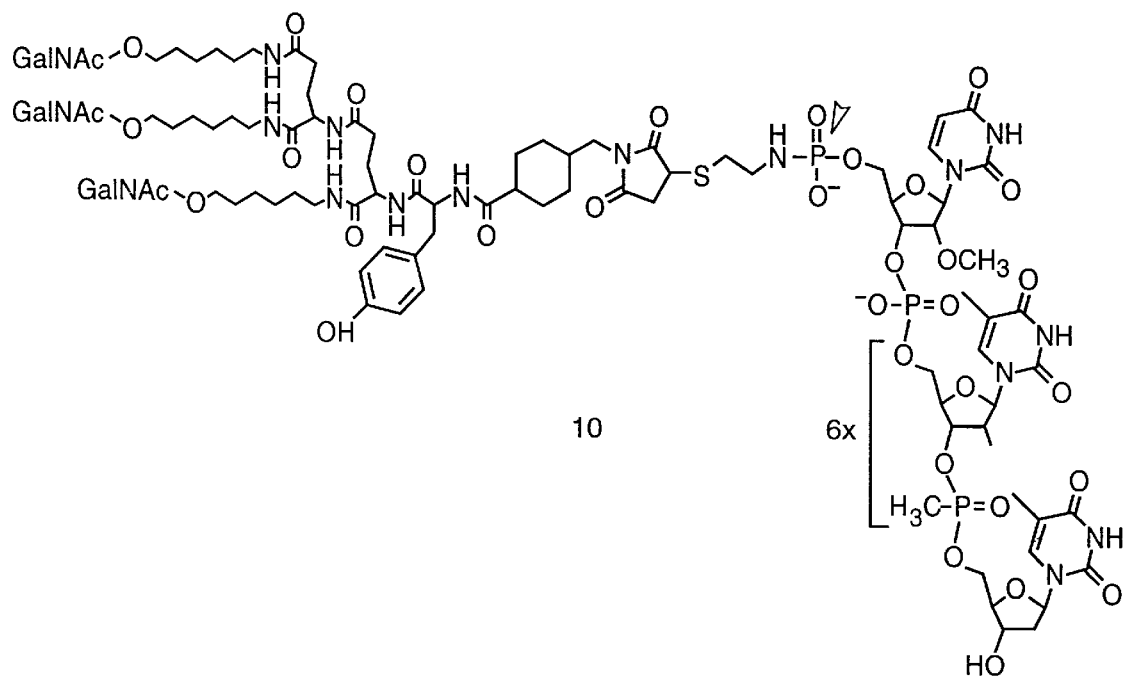
FIG. 12A: Structure of 10. The conjugate was synthesized with radioactive phosphate located on the 5'-OH of the oligoMP moiety. The arrowhead marks the position of the $^{32}$p label.
FIG. 12B: Structure of 10 written in abbreviated form. Structures 12 and 3–6 are proposed structures of metabolites identified by PAGE analysis. Structures 12 and 3–6 are obtained by treating 10 with N-acetylglucosamine, chymotrypsin or 0.1 HCl, respectively.
Figure 13:
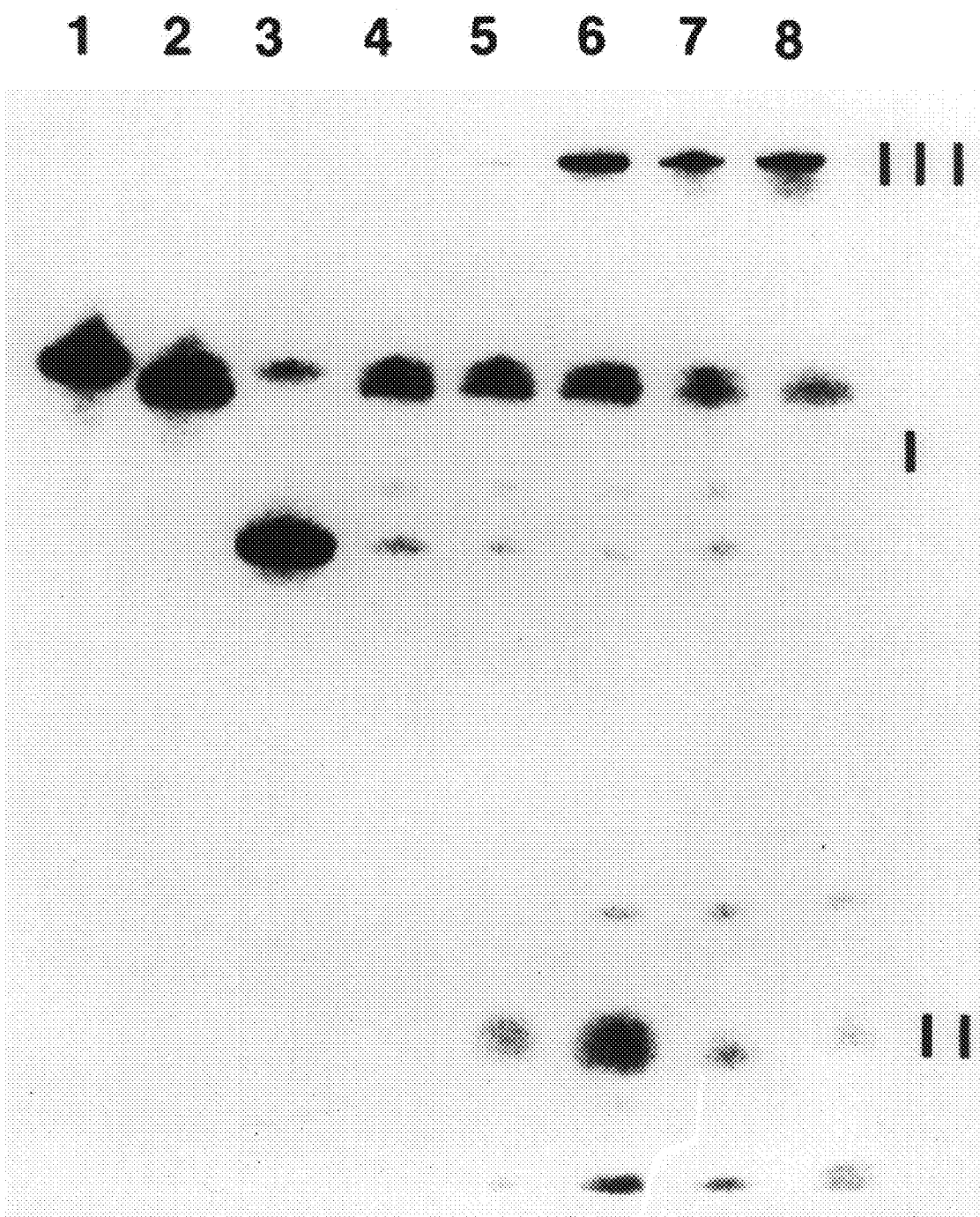
FIG. 13. Autoradiographic analysis of the metabolites of 10 in Hep G2 cells. Lane 1, 1; Lane 2, 1 treated with N-acetyl-glucosaminidase; Lane 3, 1 treated with chymotrypsin; lanes 4–8, Hep G2 cell extracts following incubation with 1 for 2, 4, 8, 16 and 24 hours respectively.

FIG. 13 shows the results of PAGE analysis of the metabolism of conjugate 10 following incubation with Hep G2 cells for 2–24 hours. Three classes of metabolites are identified (labeled I–III in FIG. 13) according to their electrophoretic mobility versus control reactions. Class I appears to consist of four chemically distinct species in which 1 and 2 predominate at all time points. Distribution of 1 and 2 is approximately 1:1 at the earliest time points shifting to predominantly 2 at longer incubation times. A third metabolite of this class (3, FIG. 12b)), which co-migrates with a material produced by chymotrypsin digestion of 1, is also observed at each time point. The relative amount of this species remains essentially constant up to the final time point (24 hour) where little remains. A fourth, unidentified species, which has slightly slower mobility than 3, is observed at all time points except for the last. All Class I metabolites appear to gradually decrease in amount by the final time point. Class II metabolites consist of radiolabeled species that have much greater electrophoretic mobility when compared to the Class I species. At least five bands are observed, however, not all of them are present at each time point. For example, bands at the positions of highest and lowest mobilities appear to increase up to the 16 hour time point than decrease at 24 hour. The same behavior is observed for the predominant species. Maximal intensity of this band occurs at 8 h followed by a gradual decrease to 24 hour. As was observed with Class I metabolites, all Class II metabolites appear to decrease in amount by the 24 hour time point. Class III metabolite(s) are largely immobile in the gel matrix and are, for the most part, retained in the well of the Polyacrylamide gel. The intensity of this band increases over time, reaching a maximal value at 24 hours.

Figure 14:
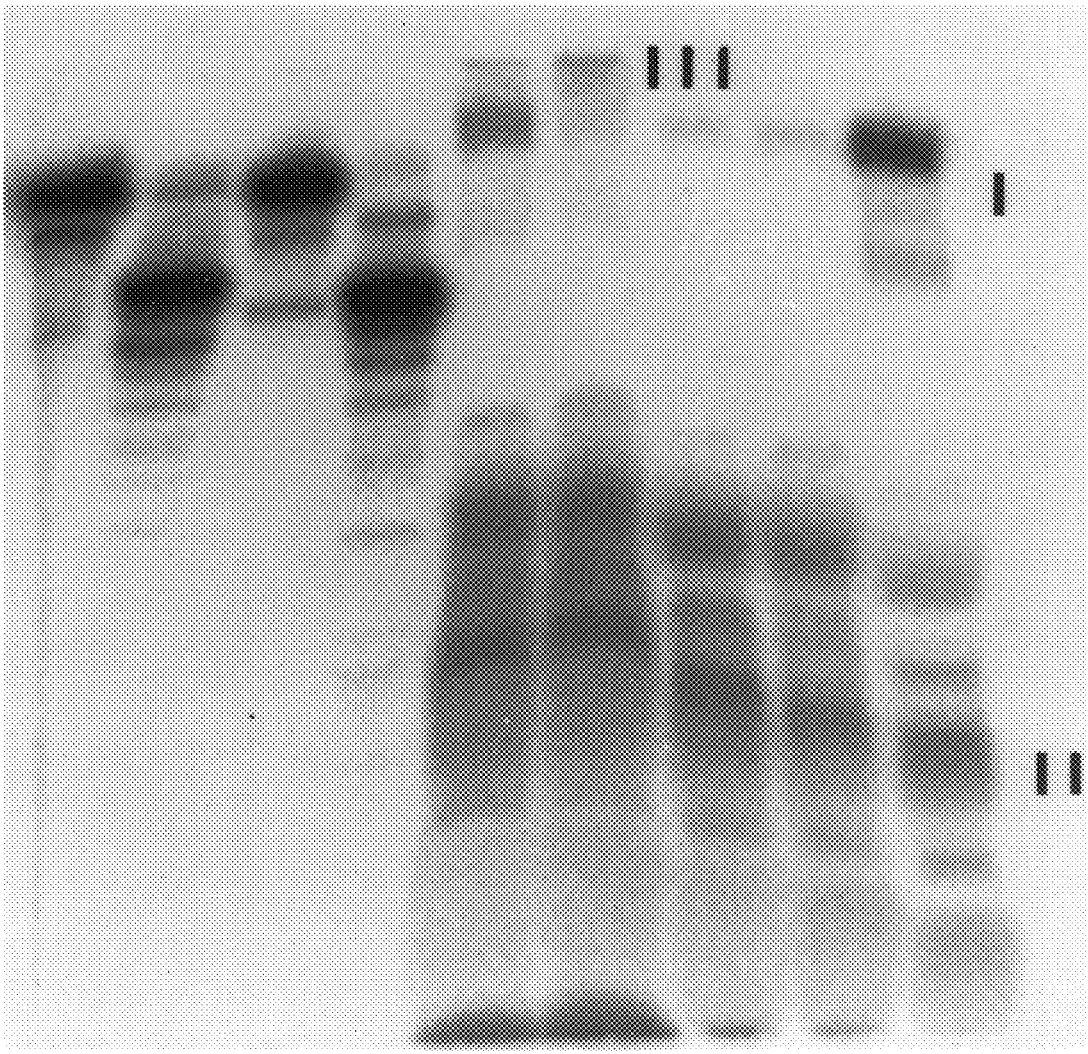
FIG. 14. Autoradiographic analysis of the metabolites of 10 in mouse liver. Lane 1, 1; Lane 2, 1 treated with N-acetyl-glucosaminidase; Lane 3, 1 treated with chymotrypsin; Lane 4, treated with 0.1 N HCl Lanes 5–9, liver homogenate extracts at 2 hours, 1 hour and 15 minutes post injection. Note that lanes 5 and 6 are replicates as well as lanes 7 and 8.

Analysis of the metabolic fate of 10 in intact mouse liver was carried out in a similar fashion. FIG. 14 shows the outcome of PAGE analysis of liver homogenate extracts obtained from liver samples of mice injected with [$^{32}$P]-labeled conjugate 10.

Following 15 minutes post-injection, there remains a significant amount of intact conjugate 10 (Class I metabolites, cf. FIG. 13). The resolution of the gel is not sufficient to permit discrimination between the two species. The remainder of the radiolabeled species in this sample migrated significantly faster than 1 and 2 and did not co-migrate with any of the controls. These metabolites appear to have a broader range of mobilities and the slowest are significantly less mobile than the Class II metabolites identified with Hep G2 cells (Class II'). At the later time points, nearly all intact 10 and 12 has disappeared, whereas the Class II' metabolites appear to increase in amount.

Figure 15:
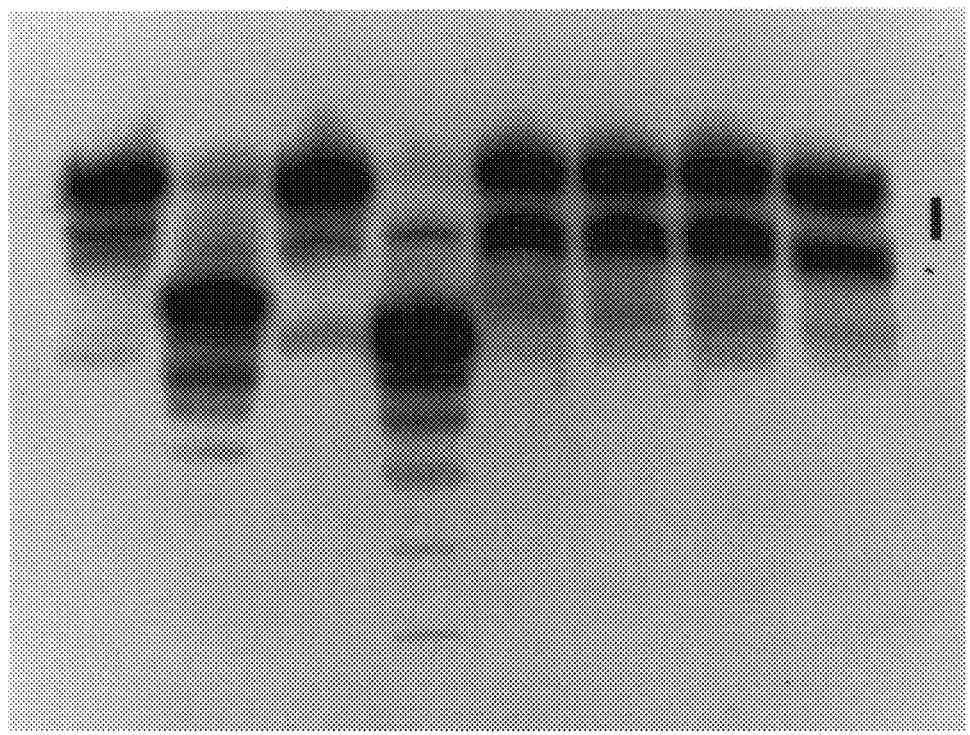
FIG. 15. Autoradiographic analysis of the metabolites of 10 in mouse urine. Lane 1, 1; Lane 2, 1 treated with N-acetyl-glucosaminidase; Lane 3, 1 treated with chymotrypsin; Lane 4, treated with 0.1 N HCl; Lanes 5–8, urine extractions at 2 hours, 1 hour and 15 minutes post injection. Note that lanes 5 and 6 are replicates.

FIG. 15 shows the pattern of metabolites observed in mouse urine following i.v. administration of the radiolabeled conjugate 10. Metabolites of Class I are the only radiolabeled species detected. The conjugate appears to be largely intact with a small but significant amount of material converted to two species, both of which do not co-migrate with any of the controls. The relative amounts of each appear to remain constant over the course of the experiment. No Class II, II' or III metabolites are observed in the mouse urine.

Discussion

The evidence described herein demonstrates that [$^{32}$P]-labeled conjugate 10, which is chemically defined and homogeneous, is capable of crossing the cellular membrane of Hep G2 cells in a manner that is both ligand and cell-type specific. A logical extension of these investigations was to determine the tissue distribution of 1 in vivo and to compare the metabolic fate of 10 in vitro and in vivo and to compare the data with those obtained with conjugate 12 which lacks the three terminal GalNAc residues.

The in vivo tissue distribution data confirm the results obtained with cultured human cells. Highly selective targeting of the oligodeoxynucleoside methylphosphonate to the liver (7±10% of i.d.) was effectively achieved through covalent attachment of the oligomer and the asialoglycoprotein receptor (ASGP) ligand, YEE(ah-GalNAc)$_3$. Indeed, the concentration of conjugate in the liver was 25-fold greater than that found in the blood and approximately 10-fold greater than in muscle based on whole tissue measurements (Table 9). These results compare favorably, and are in some ways superior, to the outcome of similar experiments reported by Lu et al., where the delivery of an [$^{32}$P]-labeled antisense oligo-dn to rat liver was enhanced when compared to other tissues owing to its complexation with an asialoglycoprotein-poly-L-lysine conjugate (Lu et al., 1994). As noted by the authors, however, the preference of the complex for the liver was marginal since the spleen, lungs and kidneys accumulated the radiolabeled oligo-dN as well (e.g., distribution for each tissue was ca. 6, 4, 2 and 2% of injected dose per gram, respectively, after 5 minutes post injection; Lu et al., 1994). It is of further interest to compare our results with those reported by Eichler et al. (1992) where the biodistribution and rate of liver uptake was determined in rats for the hypolipidaemic agent ansamycin, both alone and covalently linked to another tri-anntenary ASGP ligand, N-[tris[(b-D-galactopyranosylosy)methyl]-methyl]-N$^a$-(acetyl) glycinamide (tris-galacetate). The authors reported that the liver uptake of the free drug and the conjugate were roughly equivalent, leading them to conclude that the triantennary ASGP ligand did not enhance the uptake of the drug by rat liver. This result is in contrast to our finding that uptake by mouse hepatocytes is greatly facilitated by the covalent attachment of the ligand, YEE(ah-GalNAc)$_3$.

As a control, mice were injected with conjugate 12, which lacks the three terminal GalNAc residues, and therefore should not be recognized by ASGP receptor. As anticipated, little radioactivity was detected in the liver and a far greater amount of radioactivity was associated with other tissues (Table 11). This result extended our previous findings that the targeting of the radiolabeled oligo-MP to hepatocytes was a consequence of its covalent attachment to the ligand.

The results of this sugarless ligand-oligomer conjugate are very similar to other results which were separately reported. A tritium labelled 12 mer (d-Tp*TCCTCCTGCGG) consisting of all methylphosphonate backbone except the last 5' terminal phosphodiester linkage was injected i.v. in a single dose in mice. Organs were collected in 2, 5, 10, 30, 60 and 120 minutes after drug administration. The data shows that the radioactivity was not allocated in liver, lung, muscle or spleen, and was rapidly disappearing from the plasma into the kidney and urine. The HPLC study showed that the intact 12-mer was metabolized to 11-mer via enzymatic cleavage of the terminal nucleotide and both were eliminated rapidly into the urine after i.v. injection. Thus, the results reported herein agree well with the results obtained earlier, demonstrating the importance of the GalNAc terminal in directing the uptake of oligomer conjugate into liver.

In order to gain insight into the in vitro and in vivo metabolic fate of conjugate 10, we examined extracts obtained from Hep G2 cells grown in culture and from the liver and urine of mice by PAGE analysis. We noted that three classes of metabolites (Class I–III) were produced in Hep G2 cells and in mouse liver whereas only Class I metabolites were isolated from mouse urine. Class I metabolites appeared to arise owing to degradation of the ligand. Two enzymatic reactions were employed in an attempt to model the production of these species: N-acetylglucosamidase and chymotrypsin. The former treatment yielded 2, which migrated slightly faster than 1 due to the slight reduction in mass resulting from the loss of the three terminal GalNAc residues. The latter treatment resulted in a substantially enhanced mobility resulting from both the loss of a majority of the ligand and an increase in the overall charge from –1 to –2 (FIG. 12). These two model reactions produced compounds with modified ligands remaining covalently linked to intact radiolabeled oligo-MP. It is reasonable to conclude, therefore, that other species migrating to the same region of the gel resulted from degradation of the ligand and not from bond cleavage at other labile sites of 1. For example, hydrolysis of a single aminohexyl side chain amide bond would yield 5 (FIG. 12b) with mass between 2 and 3 and result in an increase in the negative charge from –1 to –2. In this example, a species with mobility between 2 and 3 would be expected by PAGE analysis. Class II metabolites migrate considerably faster than those identified as Class I. We propose that they arise due to unanticipated hydrolysis of the single phosphodiester linkage located at the 5'-end of the oligo-MP. It was expected that this site would be stable towards cleavage by endonuclease activity (Sproat et al., 1989) based upon a model reaction conducted with snake venom phosphodiesterase in which no cleavage was observed. Cleavage at this site would release the terminal seven nucleotides of the oligo-MP from the remainder of 1 and, most importantly, produce a relatively low molecular weight species bearing a single nucleotide containing the radiolabeled phosphate (6, FIG. 12b)). Further degradation of the ligand would produce the multiple species identified as Class II metabolites. Class III metabolites, observed in Hep G2 cells only, appear to be high molecular weight species containing radioactive phosphorous that migrate a short distance into the gel. Release of radioactive phosphate from 1 and its subsequent incorporation into high molecular weight cellular structures (nucleic acids or proteins) would account for this band. It is well documented that the endosomal compartment acidifies as it matures, reaching pH as low as 5.5 before fusing with lysosomes (Schwartz et.al., 1985) Furthermore, the phosphoramidate linkage tying the oligo-MP to the ligand is prone to hydrolysis under acidic conditions to give 4 (FIG. 12b). In order to test the possibility that acidification of the endosomal compartment resulted in the hydrolysis of the P—N bond, 1 was incubated at 37° C. in 50 mM sodium citrate at pH 5.5 and 6.0. We observed that 1 was stable at pH 6 but was substantially hydrolysed to 4 at pH 5.5 (>50%) following 24 hours and that hydrolysis occurred specifically at the phosphoramidate P—N bond as determined by PAGE analysis (data not shown). Thus, it is reasonable to conclude that incorporation of radioactive phosphate into cellular structures occurs by hydrolysis of the P-N bond due to acidification of the endosomal compartment containing 1 and release of the terminal phosphate into the cellular milleau by phosphatase activity.

The profile of metabolites observed in extracts from Hep G2 cells includes each class of metabolites. At early time points, the majority of the radioactivity is contained in Class I species, chiefly 1 and 2. At later time points, the distribution of metabolites shifts from Class I to Class II and III, where at the last time point sampled, a majority of radioactive phosphorous resides with Class III metabolites, indicating substantial hydrolysis of the P—N bond had occurred over the course of the experiment. It is readily apparent that 1 is significantly metabolized once taken into Hep G2 cells, suggesting that intracellular delivery of an antisense oligo-MP, or other agents, would be feasible by this method.

Due to the fact that only the phosphorus at the N—P bond is labeled with $^{32}$P, it is not possible to measure the metabolic fate of the oligonucleotide analoge. Since extensive metabolism of the oligonucleotide would adversely affect the ability to specifically interact with intracellular complementary nucleic acid sequences, future studies using oligonucleotide sequences labeled in other positions need to be performed.

The results of PAGE analysis of extracts obtained from mouse liver and urine demonstrate that production of metabolites in mouse liver is different from that observed with Hep G2 cells in two ways. First, digestion of 1 to produce class II' metabolites in the liver is significantly faster, with a majority of radioactivity found in these species after only 1 hour. Second, the mobility and profile of the class II' metabolites in the liver differs from the class II metabolites in the cultured cells, suggesting that the enzymatic activities encountered by 1 in mouse liver and Hep G2 cells are different. Little or no class III metabolites are produce during the 2 hour time course, a result consistent with the results from Hep G2 cells. In contrast to the extensive degradation of 1 in mouse liver, the pattern of metabolites in urine is less complex and appears to consist exclusively of Class I metabolites. The dissimilar pattern of metabolites observed for liver and urine suggest that the conjugate was delivered into liver cells and did not reside solely in the interstitial space of the organ.

Conclusions

The in vivo distribution and metabolism of a chemically defined, structurally homogeneous neoglycopeptide-oligodeoxynucleoside methylphosphonate conjugate (10) demonstrates that delivery of this conjugate is highly efficient, reaching levels of ca. 70% of the injected dose in the liver 15 minutes post injection. Together with the rapid and extensive degradation of the ligand, these results indicate that this method for the delivery of antisense agents, either methylphosphonates or other analogs, and other therapeutically useful agents will be very useful. Furthermore, these results demonstrate the potential for diagnostic imaging procedures that utilize the tissue specificity of the ligand coupled to the nucleic acid specificity of the antisense moiety, providing the means to measure regional abnormalities of cellular functions in vivo with heretofore unrealized specificity.

TABLE 9

Kinetics of [$^{32}$P]-[Yee(ah-GalNac)$_3$]-SMCC-AET-pU$^m$p$\underline{T}_7$. in mice injected i.v. at a dose level of 30 p mol.

| | percent injected dose per organ time post injection (min.) | | | | | | |
|---|---|---|---|---|---|---|---|
| Organ | 15 | 30 | 60 | 120 | 240 | 360 | 1440 |
| Blood[a] | 2.79 ± 0.18 | 2.25 ± 0.48 | 1.42 ± 0.38 | 0.90 ± 0.26 | 1.09 ± 0.16 | 1.23 ± 0.30 | 0.61 ± 0.11 |
| Liver[a] | 69.9 ± 9.9 | 41.8 ± 9.3 | 25.2 ± 2.4 | 14.2 ± 2.2 | 10.6 ± 4.2 | 8.5 ± 0.6 | 3.2 ± 1.4 |
| Spleen[a] | 0.08 ± 0.04 | 0.08 ± 0.03 | 0.2 ± 0.01 | 0.17 ± 0.04 | 0.24 ± 0.02 | 0.16 ± 0.08 | 0.25 ± 0.04 |
| Kidney[a] | 3.00 ± 1.26 | 2.12 ± 0.27 | 1.58 ± 0.15 | 1.26 ± 0.19 | 1.25 ± 0.21 | 1.80 ± 0.70 | 0.92 ± 0.19 |
| Muscle[a] | 7.83 ± 1.49 | 8.42 ± 1.51 | 8.46 ± 2.32 | 8.76 ± 0.92 | 13.0 ± 3.9 | 17.2 ± 4.6 | 13.9 ± 1.3 |
| Upper G.I. | 3.63 ± 1.85 | 12.72 ± 9.41 | 6.28 ± 1.74 | 3.73 ± 2.80 | 3.19 ± 0.78 | 3.82 ± 0.87 | 2.01 ± 0.28 |
| Lower G.I. | 0.24 ± 0.05 | 0.33 ± 0.20 | 0.38 ± 0.14 | 0.34 ± 0.05 | 0.63 ± 0.26 | 0.50 ± 0.22 | 0.48 ± 0.09 |
| Gall Bladder | 0.27 ± 0.23 | 0.62 ± 0.14 | 0.7[b] | 0.4[c] | 0.31[c] | 0.17[c] | NA |
| Feces[b] | 0.01 ± 0.01 | 0.05 ± 0.05 | 0.05 ± 0.03 | 0.27 ± 0.26 | 1.40 ± 1.11 | 0.47 ± 0.23 | 0.55 ± 0.41 |

[a]Values are reported as the average percent injected dose per organ in three animals ± one standard deviation. Approximately 0.5 microCi (30 pmol) intravenously into each mouse. The mass of each organ was determined separately and was used to determine the percent dose per organ from percent of conjugate was injected dose per gram of tissue. Typical values for the mass of each organ or tissue are:
blood = 0.07 × body mass;
liver = 1.6 + 0.21 g;
spleen = 0.17 + 0.05 g;
kidneys = 0.6 ± 0.1 g;
muscle = 0.4 × body mass.
The average body mass was 32.4 + 2.0 g (std. dev.; n = 21). The peak value of radioactivity in the urine was 27.7 ± 20.2% of injected dose at 60 minutes. The large standard deviation reflects the variation in urine production and completeness of collection between individual animals.
[b]Value is from a single determination.
[c]Value is the average of two independent determinations.

TABLE 10

Percent injected dose accumulated per organ following intravenous injection of [$^{32}$P]-[YEE(ah-GalNAc)$_3$]-SMCC-AET-pU$^m$pT$_7$.

| | percent injected dose per organ time post injection (min.) | | | | |
|---|---|---|---|---|---|
| Organ | 15 | 30 | 60 | 120 | 1440 |
| Blood[a] | 1.71 ± 0.32 | 1.55 ± 0.23 | 0.87 ± 0.12 | 1.00 ± 0.37 | 0.44 ± 0.13 |
| Liver[a] | 42.4 ± 8.0 | 28.9 ± 0.97 | 21.7 ± 3.0 | 18.6 ± 6.5 | 2.89 ± 0.45 |
| Spleen[a] | 0.04 ± 0.02 | 0.08 ± 0.01 | 0.16 ± 0.03 | 0.23 ± 0.04 | 0.30 ± 0.11 |
| Kidneys[a] | 0.93 ± 0.35 | 1.17 ± 0.11 | 1.18 ± 0.06 | 1.15 ± 0.13 | 0.68 ± 0.13 |
| Muscle[a] | 9.95 ± 1.04 | 8.37 ± 1.26 | 8.85 ± 1.30 | 8.62 ± 0.97 | 8.63 ± 1.16 |

[a]Values are reported as the average percent injected dose per organ three animals ± one standard deviation. Approximately 0.1 microCi (7 pmol) intravenously into each mouse. The following values were used to determine the percent dose per organ from percent dose per gram of tissue;
mass of blood = 0.07 × body mass;
mass of liver = 1.14 g;
mass of spleen = 0.124 g;
mass of kidneys = 0.4 g;
mass of muscle = 0.4 × body mass.
The average body mass was 23.7 + 1.2 (std. dev.; n = 15).
The peak value of radioactivity in the urine was 17.1 ± 10.2% of injected dose at 30 minutes.
The large standard deviation reflects the variation in urine production and completeness of collection between individual animals.

TABLE 11

Kinetics of [$^{32}$P]-[Yee(ah)$_3$]-SMCC-AET-pU$^m$pT$_7$. following i.v. injection.

| | percent injected dose per organ time post injection (min.). | | | | |
|---|---|---|---|---|---|
| Organ | 15 | 30 | 60 | 120 | 1440 |
| Blood[a] | 4.82 ± 0.27 | 2.35 ± 0.33 | 0.91 ± 0.43 | ND | ND |
| Liver[a] | 1.06 ± 0.21 | 1.14 ± 0.32 | 1.65 ± 0.91 | 1.38 ± 0.83 | ND |
| Spleen[a] | 0.07 ± 0.01 | 0.07 ± 0.01 | 0.12 ± 0.07 | 0.08 ± 0.08 | ND |
| Kidneys[a] | 2.46 ± 0.42 | 1.82 ± 0.03 | 0.88 ± 0.27 | 0.73 ± 0.30 | ND |
| Muscle[a] | 12.9 ± 2.1 | 13.8 ± 2.4 | 25.8 ± 18.6 | 25.3[c] | ND |

[a]Values are reported as the average of three animals ± one standard deviation. Approximately 0.1 microCi (7 pmol) of conjugate was injected intravenously into each mouse. The following values were used to determine the percent dose per organ from percent dose per gram of tissue;
mass of blood = 0.07 × body mass;
mass of liver = 1.14 g;
mass of spleen = 0.124 g;
mass of kidneys = 0.4 g;
mass of muscle = 0.4 × body mass.
The average body mass was 23.7 + 1.2 (std. dev.; n = 15).
The peak value of radioactivity in the urine was 36.9 ± 13.5% of injected dose at 30 minutes. The large standard deviation reflects the variation in urine production and completeness of collection between individual animals.
[b]Value is the average of two independent determinations.

It will be appreciated that a variety of useful compounds can be synthesized using the methods described herein, particularly with the reagents and compounds detailed in Tables 1–4. The current examples are not meant to be limiting but rather merely illustrative. It will be clear that various modifications can be made and these are intended to be included in the scope of the claimed invention.

References refered to herein are listed below for convenience and are hereby incorporated herein by reference:

1. Mirabelli, C K.; Crooke, S. T. (1993) Antisense oligonucleosides in the context of modern molecular drug discovery and development, in Antisenese research and applications (Crooke, S. T., and LeBleu, B. Ed.) CRC Press, Boca Raton, pp. 7–35.
2. Ts'o, P. O. P.; Aurelian, L.; Chang, E.; Miller, P. S. (1992) Nonionic oligodeoxynucleotide analogs (Matagen™) as anticodic agents in duplex and triplex formation. Ann. NY Acad. Sci. 600, 159–177.
3. Miller, P. S.; Mcparland, K. B.; Javaraman, K.; Ts'o, P. O. P. (1981) Biochemical and biological effects of nonionic nucleic acid methylphosphonates. Biochemistry 20, 1874–1880.
4. (a) Smith, C. C.; Aurelian, L.; Reddy, M. P.; Miller, P. S.; Ts'o, P. O. P. (1986) Antiviral effect of an oligo (nucleoside methylphosphonate) complementary to the splice junction of herpes simplex virus type 1 immediate early pre-mRNAs 4 and 5. Proc. Natl. Acad. Sci. USA 83, 2787–2791. (b) Kulka, M; Smith, C. C.; Aurelian, L.; Fishelevich, R.; Meade, K.; Miller, P.; Ts'o, P. O. P. (1989) Site specificity of the inhibitory effects of oligo (nucleoside methylphosphonate)s complementary to the acceptor splice junction of herpes simplex virus type 1 immediate early mRNA 4. Proc. Natl. Acad. Sci. USA. Biochemistry 86, 6868–6872. (c) Kulka, M.; Wachsman, M.; Miura, S.; Fishelevich, R.; Miller, P. S.; Ts'o, P. O. P.; Aurelian, L. (1993) Antiviral effect of oligo(nucleoside methylphosphonates) complementary to the herpes simplex virus type 1 immediate early mRNAs 4 and 5. Antiviral Res. 20, 115–120. (d) Kulka, M.; Smith, C. C.; Levis, J.; Fishelevich, R.; Hunter, J. C. R.; Cushman, C. D.; Miller, P. S.; Ts'o, P. O. P.; Aurelian, L. (1994) Synergistic antiviral activities of oligonucleoside methylphosphonates complementary to herpes simplex virus type 1 immediate-early mRNAs 4, 5, and 1. Antimicrobial Agents and Chemotherapy 38, 675–680.
5. Agris; C H.; Blake, K. R.; Miller, P. S.; Reddy, M. P.; Ts'o, P. O. P. (1986) Inhibition of vesicular stomatitis virus protein synthesis and infection by sequence-specific oligodeoxyribonucleoside methyphosphonates. Biochemistry 25, 6268–6275.I
6. (a) Sarin, P. S.; Agrawal, S.; Civeira, M. P.; Goodchild, J.; Ikeuchi, T.; Zamecnik (1988) Inhibition of acquired immunodeficiency syndrome virus by oligodeoxynucleoside methylphosphonates. Proc. Natl. Acad. Sci. USA 85, 7448–7451. (b) Zaia, J. A.; Rossi, J. J.; Murakawa, G. J.; Spallone, P. A.; Stephens, D. A.; Kaplan, B. E.; Eritja, R.; Wallace, R. B.; Cantin, E. M. (1988) Inhibition of human immunodeficiency virus by using an oligonucleoside methylphosphonate targeted to the tat-3 gene. J. Virology 62, 3914–3917. (c) Laurence, J.; Sikder, S. K.; Kulkosky, J.; Miller, P.; Ts'o P. O. P. (1991) Induction of chronic human immunodeficiency virus infection is blocked by a methylphosphonate oligodeoxynucleoside targeted to a U3 enhancer element. J. Virology 65, 213–219.

7. (a) Brown, D.; Zhipeng, Y.; Miller, P.; Blake, K.; Wei, C.; Kung, H.-F.; Black, R. J.; Ts'o, P. O. P., Chang, E. H. (1989) Modulation fo ras expression by anti-sense, non-ionic deoxyoligonucleotide analogs. Oncogene Research 4, 243–252. (b) Yu, Z.; Chen, D.; Black, R. J.; Blake, K.; Ts'o, P. O. P.; Miller, P.; Chang, E. H. (1989) Sequence specific inhibition of in vitro translation of mutated or normal ras p21. J. is Experimental Pathogy 4, 97–10$^7$. (c).Chang, C. H.; Miller, P. S.; Cushman, C.; Devadas, K.; Pirollo, K. F.; Ts'o, P. O. P.; Yu, Z. P. (1991) Antisense inhibition of ras p21 expression that is sensitive to a point mutation. Biochemistry 30, 8283–8286.

8. (a) Wu, G. Y.; Wu, C. H. (1987) Receptor-mediated in vitro gene transformation by a soluble DNA carrier system. J. Biol. Chem. 262, 4429 4432. (b) Wu, G. Y.; Wu, C. H. (1988) Receptor-mediated gene delivery and expression in vivo. J. Biol. Chem. 263, 14621–14624. (c) Wu, G. Y.; Wu, C. H. (1988) Evidence for targeted gene delivery to Hep G2 hepatoma cells in vitro. Biochemistry 27, 887–892. (d) Wu, G. Y.; Wu, C. H. (1992) Specific inhibition of hepatitis B viral gene expression in vitro by targeted antisense oligonucleotides. J. Biol. Chem. 267, 146–12439.

9. Plank, C.; Zatloukal, K.; Cotten, M.; Mechtler, K.; Wagner, E. (1992) Gene transfer into hepatocytes using asialoglycoprotein receptor mediated endocytosis of DNA complexed with an artificial tetra-antennary galactose ligand. Bioconjugate Chem. 3,533–539.

10. Haensler, J.; Szoka, F. C., Jr. (1993) Synthesis and characterization of a trigalactosylated bisacridine compound to target DNA to hepatocytes. Bioconjugate Chem. 4, 85–93.

11. (a) Kamen, B. A.; Wang, M. -T.; Streckfuss, A. J.; Peryea, X.; Anderson, R. G. W. (1988) Delivery of folates to the cytoplasm of MA104 cells is mediated by a surface membrane receptor that recycles. J. Biol. Chem. 263, 13602–13609. (b) Leamon, C. P.; Low, P. S. (1991) Delivery of macromolecules into living cells: a method that exploits folate receptor endocytosis. Proc. Natl. Acad. Sci. USA 88, 5572–5576. (c) Citro, G.; Szczylik, C.; Ginobbi, P.; Zupi, G.; Calabretta, B. (1994) Inhibition of leukemia cell proliferation by folic acid-polylysine-mediated introduction of c-myb antisense oligodeoxy-nucleotides into HL-60 cells. Br.J.Cancer 69, 463467.

12. Trubetskoy, V.; Torchilin, V. P.; Kennel, S. J.; Huang, L. (1992) Use of N-Terminal modified poly(L-lysine)-antibody conjugate as a carrier for targeted gene delivery in mouse lung endothial cells. Bioconjugate Chem. 3, 323–327.

13. (a) Wagner, E.; Zenke, M.; Cotten, M.; Beug, H.; Birnstiel, M. L. (1990) Transferrin-polycation conjugates as carrier for DNA uptake into cells. Proc. Natl. Acad. Sci. USA 87, 34103414. (b) Wagner, E.; Plank, C.; Zatloukal, K.; Cotten, M.; Birnstiel, M. L. (1992) Influenza virus hemagglutinin HA-2 N-terminal fusogenic peptides augment gene transfer by transferrin-polylysine-DNA complexes: Toward a synthetic virus-like gene-transfer vehicle. Biochemistry 89, 7934–7938.

14. Bonfils, E.; Dupierreux, C.; Midoux, P.; Thuong, N. T.; Monsigny, M.; Roche, A. C. (1992) Drug targeting: synthesis and endocytosis of oligonucleotide-neoglycoprotein conjugates. Nucleic Acids Res. 20, 46214629.

15. (a) Lee, R. T.; Lee, Y. C. (1987) Preparation of cluster glycosides and N-acetylgalactosamine that have sub-nanomolar binding constants toward mammalian hepatic Gal/GalNAc-specific receptors. Glycoconjugate J. 4, 317–328. (b) Oshumi, Y.; Ichikawa, Y.; Lee, Y. C. (1990) Neoglycoproteins: Recent Progress and Future Outlook. Cell Technology 9, 229–238.

16. Merwin, J. R.; Noell, G. S.; Thomas, W. C.; Chion, H. C.; De Rome, M. E.; McKee, T. D.; Spitalny, G. L.; Findeis, M. A. (1994) Targeted delivery of DNA using YEE(ah-GalNac)$_3$, a synthetic glycopeptide for the asialoglycoprotein receptor. Bioconjugate Chem. 5, 612–620.

17. (a) Miller, P. S.; Cushman, C. D.; Levis, J. T. (1991) Synthesis of oligo-2'-deoxyribonucleoside methylphosphonates, in Oligonucleotides and analogues. A practical approach (Eckstein, E., Ed.) IRL Press, Oxford, pp. 137–154. (b) Hogrefe, R. I.; Reynolds, M. A.; Vaghefi, M. M.; Yang, K. M.; Riley, K. M.; Klem, R. E.; Arnold, L. T., Jr. (1993) An improved method for the synthesis and deprotection of methylphosphonate oligodeoxynucleosides,in Methods on Molecular Biology, vol 20: Protocols for Oligonucleotides and Analogs (Aragawal, S., Ed.) Humana Press, Inc. Totown, pp. 143–164.

18. (a) Chu, B. C. F.; Wahl, G. M.; Orgel, L. E. (1983) Derivatization of unprotected polynucleotides. Nucleic Acids Res. 11, 6513–6529. (b) Chu, B. C. F.; Orgel, L. E. (1988) Ligation of oligonucleotides to nucleic acids or proteins via disulfide bonds. Nucleic Acids Res. 16, 3671–3691.

19. Gilham, P. T. (1962) Title. J. Am. Chem. Soc. 84, 687–688.

20. Ede, N. J.; Treagear, G. W.; Haralambridis, J. (1994) Routine Preparation of Thiol Oligonucleotides: Application to the Synthesis of Oligonucleotide-Peptide Hybrids. Bioconjugate Chem. 5, 373–378.

21. Wu. G. Y.; Wu, C. H., eds. (1991) Liver diseases, targeted diagnosis and therapy using specific receptors and ligands, Marcel Dekker, Inc., New York.

22. Sells, M. A.; Chen, M. L.; and Acs, G. (1987), Production of hepatitis B virus particles in HepG2 cells transfected with cloned hepatitis B virus DNA. *Proc.Natl.Acad.Sci.* 84,1005–1009.

23. Jacinta, Skelly, et al. (1979) *Nature* 282:617–618.

What is claimed is:

1. A delivery system comprising a homogeneous conjugate of formula

A—L—P wherein

A represents a carbohydrate ligand which binds specifically to a hepatic receptor, thereby facilitating the entrance of said conjugate into cells having said receptor, L represents a bifunctional linker that is chemically combined with A and P in a regiospecific manner, and P represents a biologically stable oligonucleotide or oligonucleotide derivative, wherein P is released from the conjugate following hydrolysis or reduction of specific biochemical linkages and contains internucleotide linkages resistant to enzymatic hydrolysis or biodegradation upon release from the conjugate wherein A, L, and P are covalently linked.

2. The delivery system of claim 1 wherein A is a glycosylated oligopeptide.

3. The delivery system of claim 1 wherein A is linked to L through an amide bond.

4. The delivery system of claim 1 wherein L is linked to P through a thioether bond.
5. The delivery system of claim 2 wherein A is selected from the group consisting of
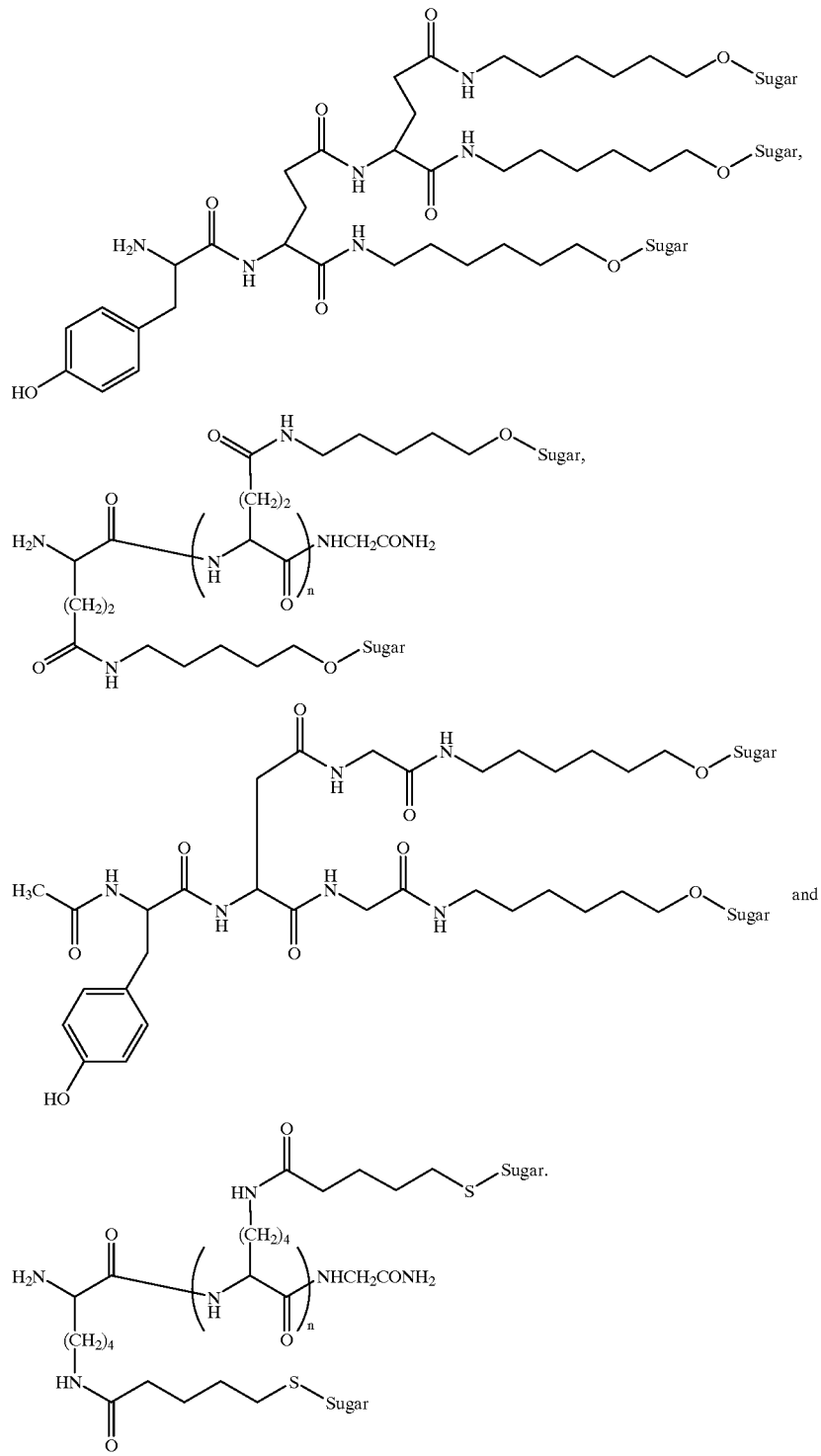

6. The delivery system of claim 5, wherein said ligand is YEE(ah-GalNAc)₃.

7. The delivery system of claim 5 wherein P is selected from the group consisting of deoxyriboside, riboside, and 2'-O-methylriboside.

8. The delivery system of claim 7 wherein P is an oligonucleoside with internucleotide linkages selected from the group consisting of phosphodiester, phosphorothionate diester, and methylphosphonate linkages.

9. The delivery system of claim 8, wherein said oligonucleotide contains alternating diester and methylphosphonate internucleotide linkages.

10. The delivery system of claim 1, wherein said oligonucleotide contains a radioactive nuclide.

11. The delivery system of claim 1 wherein P is

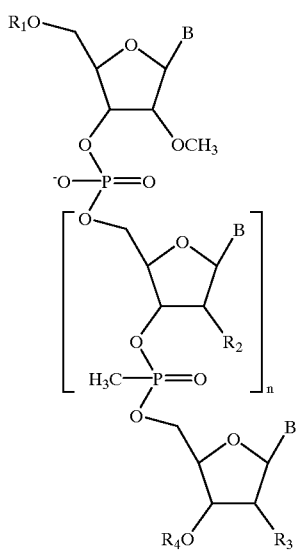

wherein B represents A, C, G or T; n is between 8 and 50, inclusive; $R_1$ is H or a 5' conjugate linkage, $R_2$ and $R_3$ are identically H or $OCH_3$, and $R_4$ is H or a 3' conjugate linkage, with the proviso that one of $R_1$ and $R_4$ is a conjugate linkage and the other is H; or

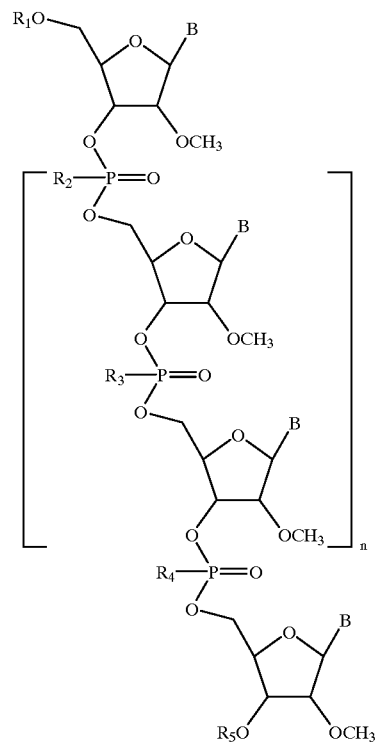

wherein B represents A, C, G or T; n is between 8 and 50, inclusive; $R_1$ is H or a 5' conjugate linkage; $R_5$ is H or a 3' conjugate linkage, $R_2$ is selected from the group consisting of $O^-$, $CH_3$, or $S^-$, wherein when $R_2$ is $O^-$, $R_3$ is $CH_3$ and $R_4$ is $O^-$;

when $R_2$ is $CH_3$, $R_4$ is $CH_3$ and $R_3$ may be $O^-$ or $S^-$;

when $R_2$ is $S^-$, $R_4$ is $S^-$ and $R_3$ may be $S^-$ or $CH_3$, with the proviso that one of $R_1$ and $R_5$ is a conjugate linkage and the other is H.

12. The delivery system of claim 1, wherein said linker is heterobifunctional.

13. The delivery system of claim 1, wherein said linker is a product of a cross-linking reagent selected from the group consisting of

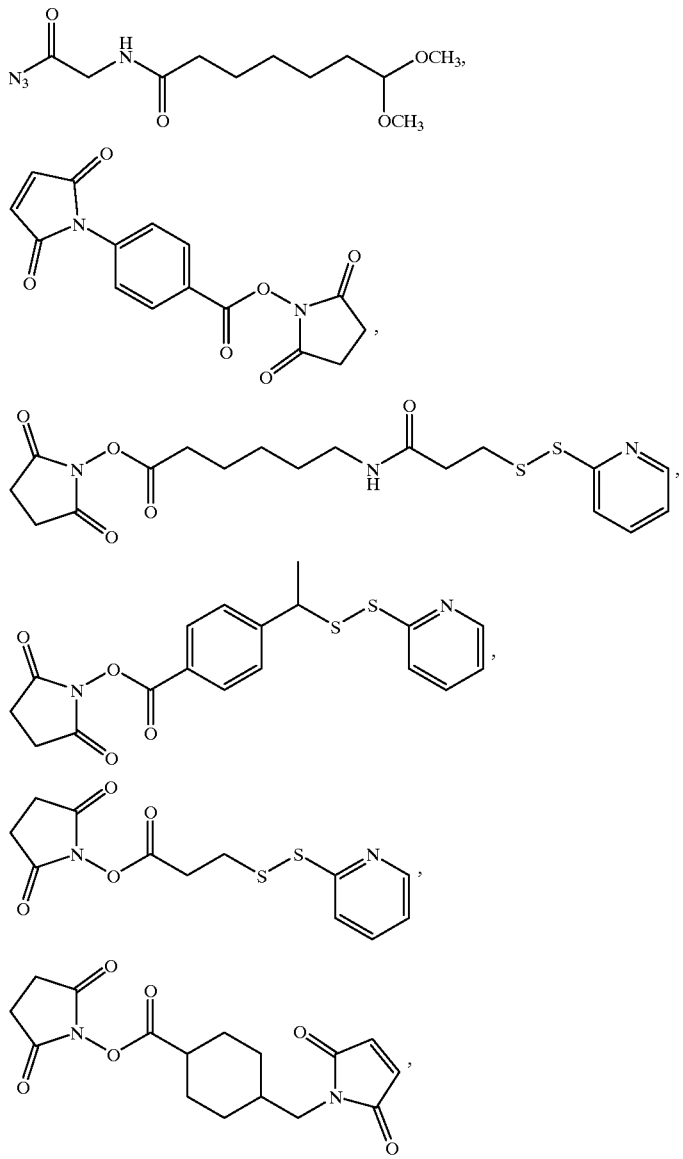

and α-citraconyl-K-(ε-FMOC)PILFFRL.

14. A delivery system comprising a homogeous conjugate of formula A—L—P, wherein A represents a hepatic ligand, L represents a bifunctional linker that 1) is covalently linked to A and P in a regiospecific manner, and 2) contains a thioether linkage and an amide linkage; and P represents a biologically stable oligonucleotide or oligonucleotide derivative, wherein P contains internucleotide linkages resistant to enzymatic hydrolysis or biodegradation upon its release from the conjugate.

15. A delivery system for tissue specific delivery to hepatic cells, said delivery system comprising a purified conjugate that contains an oligomer and a neoglycopeptide, wherein said oligomer is oligodeoxynucleoside methylphosphonate or an analog thereof, and wherein said oligomer and said neoglycopeptide are covalently linked by a bifunctional linker.

16. The delivery system of claim 15 which is gene specific.

17. The oligodeoxynucleoside methylphosphonate neoglycopeptide conjugate [YEE(ah-GalNAc)$_3$]-SMCC-AET-U'''pT$_7$.

* * * * *